US007868224B2

(12) United States Patent
Bate et al.

(10) Patent No.: US 7,868,224 B2
(45) Date of Patent: Jan. 11, 2011

(54) COMPOSITIONS AND METHODS FOR INCREASING PLANT TOLERANCE TO HIGH POPULATION DENSITY

(75) Inventors: Nicholas J Bate, Urbandale, IA (US); Milo J Aukerman, Newark, DE (US)

(73) Assignees: Pioneer Hi-Bred International, Inc., Johnston, IA (US); E.I. Du Pont de Nemours & Co., Wilmington, DE (US)

( * ) Notice: Subject to any disclaimer, the term of this patent is extended or adjusted under 35 U.S.C. 154(b) by 773 days.

(21) Appl. No.: 11/682,909

(22) Filed: Mar. 7, 2007

(65) Prior Publication Data
US 2008/0235827 A1    Sep. 25, 2008

Related U.S. Application Data

(60) Provisional application No. 60/779,720, filed on Mar. 7, 2006.

(51) Int. Cl.
*C12N 15/82* (2006.01)
*C12N 15/29* (2006.01)
*A01H 5/00* (2006.01)
*A01H 5/10* (2006.01)

(52) U.S. Cl. .................. 800/278; 800/290; 800/287; 800/298; 800/320.1; 800/312; 536/23.1; 536/23.6; 435/320.1

(58) Field of Classification Search ................. None
See application file for complete search history.

(56) References Cited

U.S. PATENT DOCUMENTS

| | | | |
|---|---|---|---|
| 6,433,251 B1 | 8/2002 | Wagner et al. | |
| 6,689,940 B2 * | 2/2004 | Wagner et al. | 800/298 |
| 6,903,192 B2 | 6/2005 | Wagner et al. | |
| 7,053,182 B2 | 5/2006 | Wagner et al. | |
| 2006/0277633 A1 | 12/2006 | Wagner et al. | |

FOREIGN PATENT DOCUMENTS

WO    0009658 A2    2/2000

OTHER PUBLICATIONS

Covington et al (2001, The Plant Cell 13:1305-1315).*
Liu et al (2001, The Plant Cell 12:1293-1304).*
Liu, X, et al.; "ELF3 Encodes a Circadian Clock-Regulated Nuclear Protein That Functions in an *Arabidopsis* PHYB Signal Transduction Pathway"; The Plant Cell (Jun. 2001) 13:1293-1304; American Society of Plant Physiologists; Rockville, MD, US.
Garg, A., et al.; "Light-regulated overexpression of an *Arabidopsis phytochrome* A gene in rice alters plant architecture and increases grain yield"; Planta (2006) 223:627-636; Springer-Verlag; Berlin/Heidelberg, Germany.
Roux, F., et al.; "How to be early flowering: an evolutionary perspective"; Trends in Plant Science (2006) 11 (8):375-381; Elseiver Ltd., Oxford, UK.
Pagano, E., et al.; "Intra-specific competition in maize: Early established hierarchies differ in plant growth and biomass partitioning to the ear around silking"; Field Crops Research (2007) 101:306-320; Elseiver Ltd., Oxford, UK.
Robson, P., et al.; "Genetic engineering of harvest index in tobacco through overexpression of a phytochrome gene"; Nature Biotechnology (Aug. 1996) 14:995-998; MacMillan Publishers Ltd; US.
Sawers, R., et al.; "Cereal phytochromes: targets of selection, targets for manipulation?"; Trends in Plant Science (Mar. 2005) 10(3):138-143; Elseiver Ltd., Oxford, UK.
Franklin, K., et al.; "Phytochromes and Shade-avoidance Responses in Plants"; Annals of Botany (2005) 96:169-175; Oxford University Press; Oxford, UK.
XP-002460248 Database Geneseq Accession No. AB024035; Mar. 5, 1999; "Structural analysis of *Arabidopsis thaliana* chromosome 5, X. Sequence features of the regions of 3,076,755 bp coverd by sixty P1 and TAC clones"; DNA Res. 7(1):31-63 (2000).
XP-002460248 Database Geneseq Accession No. AB024035; Oct. 1, 2000; "Structural analysis of *Arabidopsis thaliana* chromosome 5, X. Sequence features of the regions of 3,076,755 bp coverd by sixty P1 and TAC clones"; DNA Res. 7(1):31-63 (2000).
XP-002460247 Database Geneseq Accession No. CC169680; Apr. 30, 2003; "Genomic shotgun sequences from Zea mays (methyl filtered)".
Oda, A., et al.; "Antisense suppression of the *Arabidopsis* PIF3 gene does not affect circadian rhythms but causes early flowering and increases FT expression"; FEBS Letters (2004) 557:259-264; Blackwell Publishing Ltd; Oxford, UK.
Cerdan, P., et al.; "Regulation of flowering time by light quality"; Nature (Jun. 19, 2003) 423:881-885; Nature Publishing Group; London, UK.
Salter, M., et al.; "Gating the rapid shade-avoidance response by the circadian clock in plants"; Nature (Dec. 11, 2003) 426:680-683; Nature Publishing Group; London, UK.

(Continued)

*Primary Examiner*—Stuart F. Baum

(57) ABSTRACT

Compositions and methods for suppressing the shade-avoidance response of plants and improving plant yield are provided. Compositions of the invention include an early flowering 3 (ELF3) maize gene, the promoter for this gene, an *Arabidopsis* basic helix-loop-helix transcription factor (bHLH-041), and fragments and variants thereof. The ELF3 promoter sequence is useful for driving expression of polynucleotides of interest in a plant. The ELF3 and bHLH-041 sequences of the invention, or variants and fragments thereof, are provided in expression cassettes for use in manipulating expression of the ELF3 and bHLH-041 genes. By increasing expression of ELF3 and/or suppressing expression of bHLH-041, the methods of the invention provide for altered response of a plant to light quality and suppression of the high-density-invoked survival mode of development. The invention thus provides methods for growing crop plants at high population densities for yield enhancement. Transformed plants having the altered shade-avoidance phenotype of the invention, and seeds of said plants, are also provided.

13 Claims, 8 Drawing Sheets

OTHER PUBLICATIONS

Hicks, K., et al.; "Early Flowering3 Encodes a Novel Protein That Regulates Circadian Clock Function and Flowering in *Arabidopsis*"; The Plant Cell (Jun. 2001) 13:128-1292; American Society of Plant Physiologists, Rockville, MD, US.

Covington, M., et al.; "ELF3 Modulates Resetting of the Circadian Clock in *Arabidopsis*"; The Plant Cell (Jun. 2001) 13:1305-1315; American Society of Plant Physiologists, Rockville, MD, US.

Toledo-Ortiz, G., et al.; "The *Arabidopsis* Basic/Helix-Loop-Helix Transcription Factor Family"; The Plant Cell (Aug. 2003) 15:1749-1770; American Society of Plant Physiologists, Rockville, MD, US.

Boccalandro, H., et al.; "Increased Phytochrome B Alleviates Density Effects on Tuber Yield of Field Potato Crops"; Plant Physiology (Dec. 2003) 133:1539-1546; American Society of Plant Biologists, Rockville, MD US.

Boylan, M., et al.; "Phytochrome A overexpression inhibits hypocotyl elongation in transgenic *Arabidopsis*"; Proc Natl Acad Sci USA (Dec. 1991) 88:10806-10810; National Academy of Sciences, Washington, DC US.

Chory, J., et al.; "From seed germination to flowering, light controls plant development via the pigment phytochrome"; Proc Natl Acad Sci USA (Oct. 1996) 93:12066-12071; National Academy of Sciences, Washington, DC US.

Blazquez, M.; "Flower development pathways" J Cell Sci (2000) 113:3547-3548; The Company of Biologists Ltd., Cambridge, UK.

UNIPROT Database Accession No. Q9LTS4; Oct. 1, 2000.

* cited by examiner

Figure 1. Alignment of maize, rice, and Arabidopsis ELF3 sequences, and consensus.

```
ZM-ELF3-X           (1)  --MTRGGGQGGKEEPGKVMGPLFPRLHVSDAGKGGGPRAPPRNKMALYEQFTVPSNRFSSPAA
OS-ELF3 BAA83571    (1)  MATRGGGGGGGKEAAKGKVMGPLFPRLHVNDAAKGGGPRAPPRNKMALYEQFTVPSHRFSGGGG
ELF3 At2g25930      (1)  -------MKRGK-DEEKILEPMFPRLHVNDADKGG-PRAPPRNKMALYEQLSIPSQRFGDHGT
Consensus           (1)          GGKED GKVMGPLFPRLHVNDAAKGGGPRAPPRNKMALYEQFTVPSNRFS  GA Zm  SARAAG------ASLVPSTAAAQVYGYDRTLFQPFDVPSNEPPRSSEKFKGNTINGQSNSTRREPLRMSSQTKNKDVCASKSIA
Os  GGGVGGSPAHSTSAASQSQSQSQVYGRDSSLFQPFNVPSNRPGHSTEKINSDKINKKISGSRKELGMLSSQTKGMDIYASRSTA
At  MNSRSNN----TSTLVHPGPSSQPCGVERNLSVQHLDSSAAN---------------------------------QATEKFVS
Cs             AAG    TSSLV S AASQVYG DRSLFQPF VPSN P SSEK       IN        SRKE    LSSQTK   DI ASKSIA Zm  KCTSQHRVGNTIMSS-GKKVVSDDEFMVPSICYPRFYRQSTQDHA----DKSKPQSTTNPHKSP AMSKSSVECYSTVNKHLDK
Os  EAP-QRRAENTIKSSSGKRLADDDEFMVPSVFNSRFPQYSTQENAGVQ-DQSTPLVAANPHKSPSTVSKSSTKCYNTVSKKLER
At  QMSFMENVRSSAQHDQRKMVREEEDFAVPVYINSRRSQSHGRTKSGIEKEKHTPMVAPSSHHSIRFQEVNQTGSKQNVCLATCS
Cs   S Q RV NTI SS GKKV DDDEFMVPSI NSRF Q STQD AGI  DKSTPLVA NPHKSP MSKSST CYNTV K LDK Zm  INEAGRRLMNSPKVKEKEAVQGSKGVEVEKSSSFQAS---ENFKDKYAKLCQMRNKASNIN-----HCDNNGCQPASVNGNFT
Os  IHVSDVKSRTPLKDKEMEAAQTSKNVEVEKSSSFHASK---DMFESRHAKVYPKMDKTGIINDSDEPHGGNSGHQATSRNGGSM
At  KPEVRDQVKAN---ARSGGFVISLDVSVTEEIDLEKSASSHDRVNDYNASLRQESRNRLYRDG------GKTRLKDTDNGAES
Cs  I EA  KLK  K KE EA Q SK VEV E SS   S     D F DKHA L Q    K YIN    H  N G Q  S NGA  S Zm  EAKNPTAARNTSFCKPCTDVDSSNRKSNLLERSPREVGAKRK------------RGHHNGEQNDDLSDSSVECIPGEEI
Os  KFQNPPMRRNEISSNPSS--ENTDRHYNLPQGGIEETGTKRKRLLEQHDAEKSDDVSRLLEQHDAENIDDVSDSSVECITGWEI
At  HLATENHSQEGHGSPEDIDNDREYSKSRACAS-----------------------LQQINEEASDDVSDDSMVDSISSIDV
Cs         NP  ARN    S P SD D S RKSNL         E G KRK              L    HDAEN DDLSDSSVECISG EI Zm  SPDEIVAAIGPKHFWKARRAIQNQQRVFAVQVFELHKLIKVQKLIAASPHLLIEGDPVLGNALTGK--RNKLPKGNSK----V
Os  SPDKIVGAIGTKHFWKARRAIMNQQRVFAVQVFELHKLVKVQKLIAASPHVLIESDPCLGNALLGS---KNKLVEENLK----A
At  SPDDVVGILGQKRFWRARKAIANQQRVFAVQLFELHRLIKVQKLIAASPDLLLDEISFLGKVSAKSYPVKKLLPSEFLVKPPLP
Cs  SPDDIVGAIG KHFWKARRAI NQQRVFAVQVFELHKLIKVQKLIAASPHLLIE DP LGNAL GS    KNKLP  ENLK
```

Figure 1. Alignment of maize, rice, and Arabidopsis ELF3 sequences, and consensus.

```
Zm  RTLSITNKDDIQPTLEQPELSKQDTEGNLLAHSHDGGLGDNHHNQAATNEIFTSNPPAMPVAPDNKQNNWCMNP--PQ
Os  QPLLVATIDDVEPSLQQPEVSKENTEDSPPSP-HDTGLGSGQRDQAATNGVSKSNRRATPVASDNKQNNWGVQLQPPQ
At  HVVVKQRGDSEKTDQHKMESSAENVVGRLSNQ-------GHHQQSNYMPFANNPPASPAPNGYCFPPQPPPS-GNH
Cs       LLI    DDI PSL QPELSKENTEG L A    HD GLG   H QAATN IF SNPPASPVA DNKQNNW MN   PQ

Zm  NQWLVPVMSPSEGLVYKPFAGPCPPVGNLLTPFYANCTPLRLPSTP-------YGVPIPHQPQHMVPPGAPAMHMNY
Os  NQWLVPVMSPLEGLVYKPYSGPCPPAGSILAPFYANCTPLSLPSTAGDFMNSAYGVPMPHQPQHMGAPGPPSMPMNY
At  QQWLIPVMSPSEGLIYKPHPGMAHTGHYG--GYYGHYMPT--P------------MVMPQYHPGMGFPPPG-----NGY
Cs  NQWLVPVMSPSEGLVYKPHAGPCPPAG   IL PFYANCTPL LPST        YGVPIPHQPQHM PPG PAM MNY

Zm  FPPFSMP--VMNPGTPASAVEQGSHAAAPQPHGHMDQQSLISCNMSHPSGVWRFLASRDSEPQASSATSPFDRLQVQ
Os  FPPFSIP--VMNPTAPAPVVEQGRHPSMPQPYGNFEQQSWISCNMSHPSGIWRFHASRDSEAQASSASSPFDRFQCS
At  FPPYGMPTIMNPYCSSQQQQQ------QPNEQMNQFGHPGNLQNTQQQQRS-DNEPAPQQQQQPTKSYPRARKS
Cs  FPPFSMP  VMNP   PA   VEQG H A  PQPHGNMDQQS ISCNMSHPSGIWRF ASRDSE QASSATSPFDR Q S

Zm  GDGSAPLSLLSFFPTASAPNVQPPPSSGGWDRDQQNHVIRVVPRNAQTASVPKAQPQPSSGGRDQKNHVIRVVPHNAQ
Os  GSG-----PVSAFPTVSAQNNQP------------------QP--SYSSRDNQTNVIKVVPHNSR
At  RQGSTGSSPSGPQGISGSKSFRPFAAVDEDSNINN----APEQTMTTTTTTRTTVTQTTRDGGVTRVIKVVPHNAK
Cs  G GS   SPLS FPTASA N QP A              NN           T S K QP SS  RDN T VIKVVPHNAK

Zm  TASESAAWIFRSIQMERNQNDS---
Os  TASESAARIFRSIQMERQRDD----
At  LASENAARIFQSIQEERKRYDSSKP
Cs  TASESAARIFRSIQMERNR DS
```

FIGURE 3A

*Arabidopsis thaliana* "evening element"

```
 32   CTGGCCCGAAAAGTCCGGCC
 92   GTTACCTAAAATTTATCTA
103   ATTTATCTAAAAACACTATT
140   CTATTGGTAAAATAGAGTTT
180   ATAACCTTAAAAGAGTAAG
237   CACACCCCAAAAAAACCTGC

GTCCCGTCAAAATATCTCGC
```

FIGURE 3B

```
  1   CGAGGGGCTC CTATTTTCGG ACCGTGCTCG TGCTGGCCCG AAAAGTCCGG CCCATATTCC CAGCACTAGA
 70   CATGACATTA CCATCTGTAG CAGTTTACCT AAAATTTATC TAAAAACACT ATTTTTCACT ATAAACTTCA
141   CTATTGGTAA AATAGAGTTT AAATATTGGT GAGTTGAAG  ATAACCTTAA AAAGAGTAAG TTGTTAGAAC
211   TTAGAAGCAA CCTCACCGCC TAATTAACAC ACCCCAAAAA AACCTGCTTG CACATACTCA ACCGCCAGCG
281   TCTCCACTCT CGGTCTCCCC TCTCATGGTG GAGCCCACCT CGGCCTTTGT GGATCAGAGC GAGCATTCCT
351   TTCCCTTCCC TTCCCTGGCA TCAGAATCAA ACGTGTCCCC GCAGACGCTC CCAATCCCAT GCGCCCCTCT
421   GCTCTCACGG TTTGATTTCC CTTTCAGTTG GGCCGCCATG GCCCGGGTAG CAGCTGTGCG CCTGCACCCC
491   GGCCTCCCCC ATCGCCGGCC TGACACTGG  GTAAACGTGG TGGCTGAAGC TGCTGCTGAG GATTCGGGAT
561   CTTCTTGCTG CCGCCACGAG CTGCCCTGCG GATATTGACA CGGCGCGCTC CCCTGGCTCC TGGGC
```

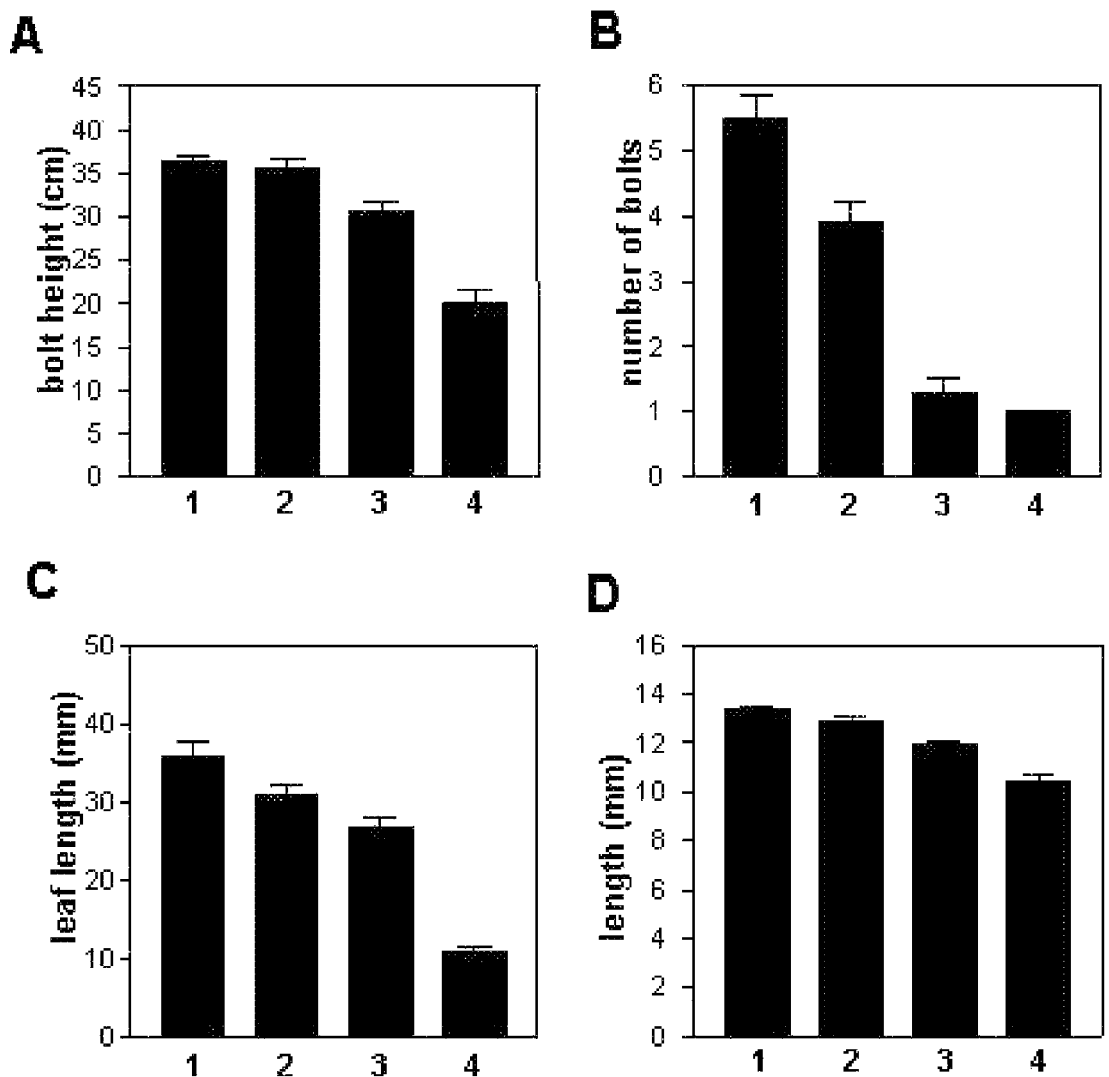
Fig. 4. Quantification of the density response in Arabidopsis.

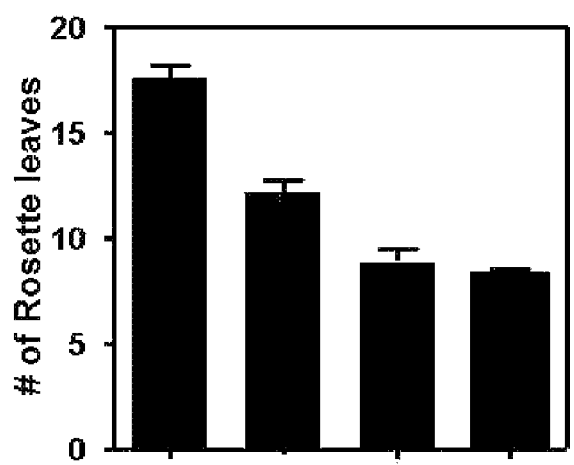
Fig 5. Effect of planting density on flowering time in interplanted Arabidopsis.

A
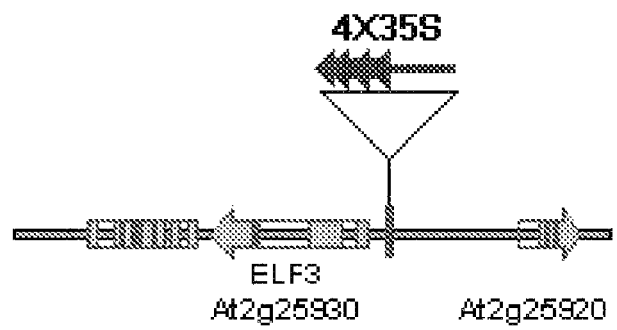
B
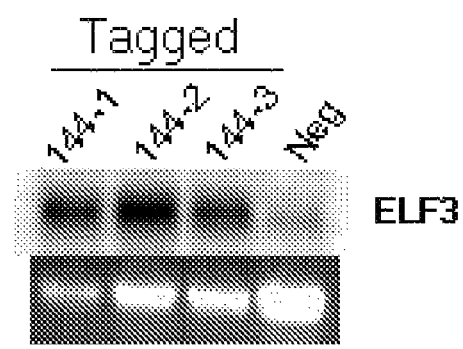
C
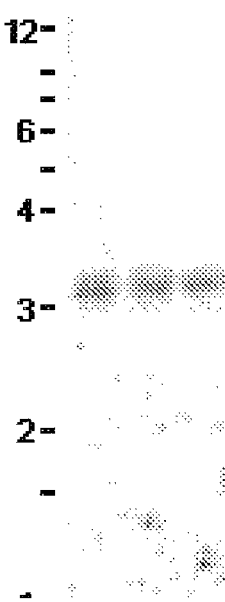
Figure 6. Activation tagging of ELF3 mutant.

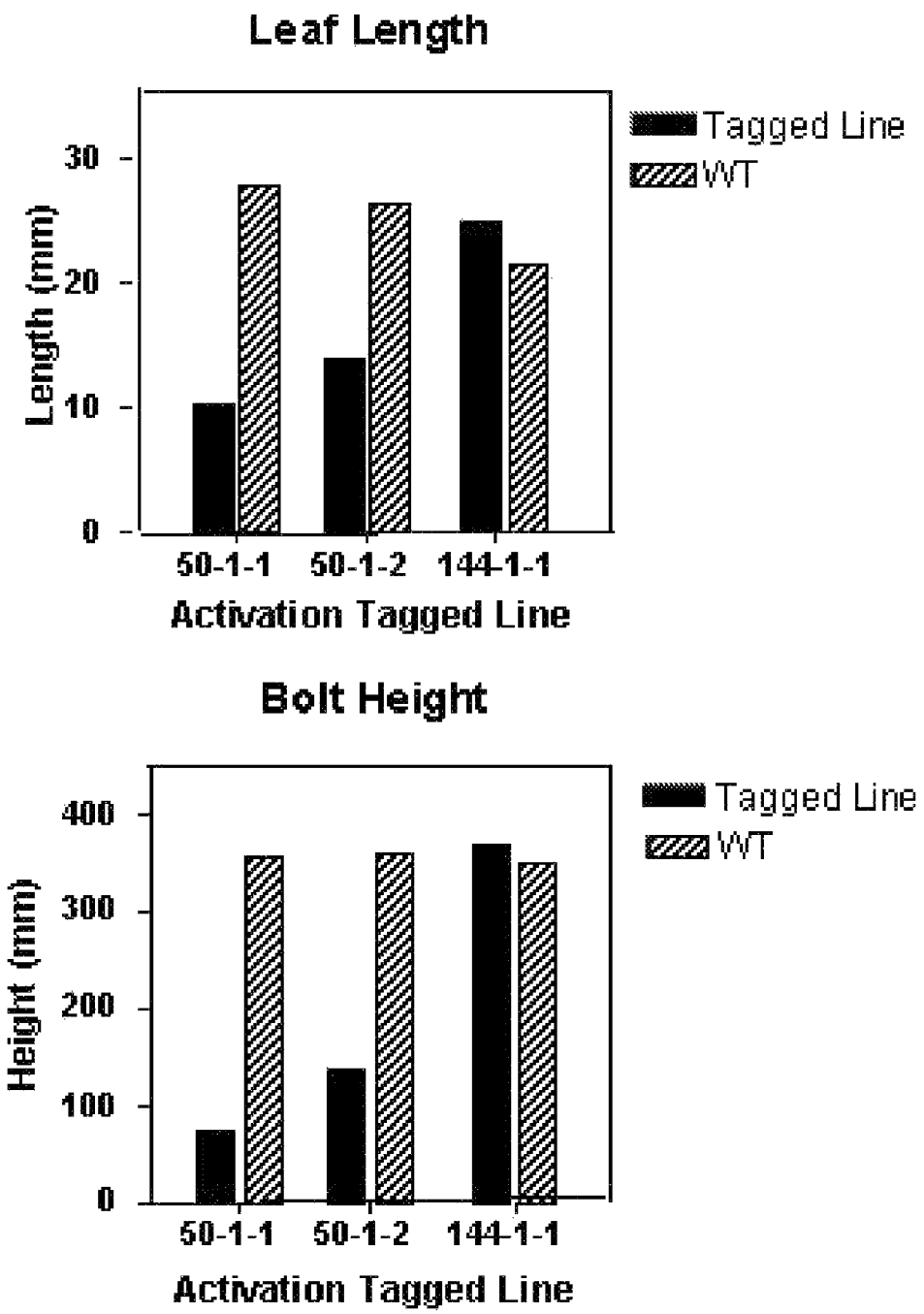
Fig. 7. Effect of density on activation-tagged lines in an interplanting experiment.

```
                           SEQUENCE LISTING

<160> NUMBER OF SEQ ID NOS: 10

<210> SEQ ID NO 1
<211> LENGTH: 2496
<212> TYPE: DNA
<213> ORGANISM: Zea mays
<220> FEATURE:
<221> NAME/KEY: CDS
<222> LOCATION: (167)...(2444)
<223> OTHER INFORMATION: Zm-ELF3

<400> SEQUENCE: 1
ggccgcggta gcagctgtgc gcctgcaccc cggcctcccc catcgccggc cctgacactg      60
ggtaaacgtg gtggctgaag ctgctgctga ggattcggga tcttcttgct gccgccacga     120
gctgcctgcg tgatattgac acggcgcgct ccctggctc ctgggc atg acg agg         175
                                                 Met Thr Arg
                                                   1 gga ggc ggt gga caa gga ggc aag gag gag ccg ggg aag gtg atg ggt       223
Gly Gly Gly Gly Gln Gly Gly Lys Glu Glu Pro Gly Lys Val Met Gly
      5                  10                  15 ccg ctg ttc ccg cgg ctc cac gtc agc gac gca ggc aag ggc ggc ggc       271
Pro Leu Phe Pro Arg Leu His Val Ser Asp Ala Gly Lys Gly Gly Gly
 20                  25                  30                  35 ccg cgg gct ccg ccc agg aac aag atg gcg ctc tac gag cag ttc acc       319
Pro Arg Ala Pro Pro Arg Asn Lys Met Ala Leu Tyr Glu Gln Phe Thr
                 40                  45                  50 gtg ccg tcc aac cgc ttc agc tcc ccc gcc gcc tcc gcc cgc gcc gcg       367
Val Pro Ser Asn Arg Phe Ser Ser Pro Ala Ala Ser Ala Arg Ala Ala
             55                  60                  65 ggg gcc agc ctc gtg ccc tcc acg gcg gct gcc cag gtt tat ggt tat       415
Gly Ala Ser Leu Val Pro Ser Thr Ala Ala Ala Gln Val Tyr Gly Tyr
         70                  75                  80
```

-continued

| | |
|---|---|
| gac agg acg ctg ttc cag ccc ttc gat gtg cct tca aat gag cct cct<br>Asp Arg Thr Leu Phe Gln Pro Phe Asp Val Pro Ser Asn Glu Pro Pro<br>85                       90                       95 | 463 |
| cgt tca tct gaa aag ttc aaa gga aac act atc aac gga cag tct aat<br>Arg Ser Ser Glu Lys Phe Lys Gly Asn Thr Ile Asn Gly Gln Ser Asn<br>100                    105                    110                    115 | 511 |
| agt aca aga aga gaa cct ttg agg atg tcc tca cag acc aag aac aag<br>Ser Thr Arg Arg Glu Pro Leu Arg Met Ser Ser Gln Thr Lys Asn Lys<br>                  120                    125                    130 | 559 |
| gac gtc tgt gct tca aaa tca att gcc aag tgc acc tca cag cat aga<br>Asp Val Cys Ala Ser Lys Ser Ile Ala Lys Cys Thr Ser Gln His Arg<br>             135                    140                    145 | 607 |
| gtg ggc aac acc atc atg tct tct ggg aag aaa gtg gtc agt gat gat<br>Val Gly Asn Thr Ile Met Ser Ser Gly Lys Lys Val Val Ser Asp Asp<br>150                    155                    160 | 655 |
| gaa ttt atg gtt cct tcc atc tgt tat cct aga ttt tat cga cag tct<br>Glu Phe Met Val Pro Ser Ile Cys Tyr Pro Arg Phe Tyr Arg Gln Ser<br>165                    170                    175 | 703 |
| act caa gat cat gca gat aaa tca aaa ccc caa tct act aca aac cca<br>Thr Gln Asp His Ala Asp Lys Ser Lys Pro Gln Ser Thr Thr Asn Pro<br>180                    185                    190                    195 | 751 |
| cac aaa agt cct gca atg tcc aaa tca tct gta gag tgc tat agt act<br>His Lys Ser Pro Ala Met Ser Lys Ser Ser Val Glu Cys Tyr Ser Thr<br>                  200                    205                    210 | 799 |
| gtg aac aag cac ttg gac aaa atc aat gaa gct ggt agg agg tta atg<br>Val Asn Lys His Leu Asp Lys Ile Asn Glu Ala Gly Arg Arg Leu Met<br>             215                    220                    225 | 847 |
| aac tct cca aag gtt aag gag aaa gaa gca gtg caa gga tca aaa ggt<br>Asn Ser Pro Lys Val Lys Glu Lys Glu Ala Val Gln Gly Ser Lys Gly<br>230                    235                    240 | 895 |
| gtg gaa gtt aaa gaa aag agt tca tca ttt cag gca tca gaa aat ttc<br>Val Glu Val Lys Glu Lys Ser Ser Ser Phe Gln Ala Ser Glu Asn Phe<br>245                    250                    255 | 943 |
| aaa gac aaa tat gct aag cta tgt caa atg agg aat aag gca agt aat<br>Lys Asp Lys Tyr Ala Lys Leu Cys Gln Met Arg Asn Lys Ala Ser Asn<br>260                    265                    270                    275 | 991 |
| ata aat cat tgt gac aac aac ggt tgc caa cct gca agc gtg aat gga<br>Ile Asn His Cys Asp Asn Asn Gly Cys Gln Pro Ala Ser Val Asn Gly<br>                  280                    285                    290 | 1039 |
| aat ttc aca gaa gca aag aac cct aca gca gct aga aat aca tct ttc<br>Asn Phe Thr Glu Ala Lys Asn Pro Thr Ala Ala Arg Asn Thr Ser Phe<br>             295                    300                    305 | 1087 |
| tgt aaa cca tgt act gat gta gat agc tct aac agg aag tct aat tta<br>Cys Lys Pro Cys Thr Asp Val Asp Ser Ser Asn Arg Lys Ser Asn Leu<br>310                    315                    320 | 1135 |
| ctg gaa aga agc cca cgg gaa gtt ggt gct aag aga aaa aga gga cat<br>Leu Glu Arg Ser Pro Arg Glu Val Gly Ala Lys Arg Lys Arg Gly His<br>325                    330                    335 | 1183 |
| cac aat gga gag caa aat gat gat tta tct gac tcc tca gtg gaa tgc<br>His Asn Gly Glu Gln Asn Asp Asp Leu Ser Asp Ser Ser Val Glu Cys<br>340                    345                    350                    355 | 1231 |
| ata cct ggg gag gag atc tct cca gat gaa att gtt gct gct att ggt<br>Ile Pro Gly Glu Glu Ile Ser Pro Asp Glu Ile Val Ala Ala Ile Gly<br>                  360                    365                    370 | 1279 |
| cca aag cat ttc tgg aaa gcg aga aga gct att cag aat cag cag agg<br>Pro Lys His Phe Trp Lys Ala Arg Arg Ala Ile Gln Asn Gln Gln Arg<br>             375                    380                    385 | 1327 |
| gtt ttt gct gtc caa gtg ttc gag ctg cat aag ctg ata aaa gtg cag<br>Val Phe Ala Val Gln Val Phe Glu Leu His Lys Leu Ile Lys Val Gln | 1375 |

-continued

```
                390                 395                 400
aag tta atc gcg gca tct cca cat ctg ctt att gaa ggt gat cct gtc    1423
Lys Leu Ile Ala Ala Ser Pro His Leu Leu Ile Glu Gly Asp Pro Val
        405                 410                 415 ctt ggc aat gca tta aca gga aaa agg aac aag ctt cct aaa gga aat    1471
Leu Gly Asn Ala Leu Thr Gly Lys Arg Asn Lys Leu Pro Lys Gly Asn
420                 425                 430                 435 tcg aaa gtt cgg acc ctg tca atc aca aac aaa gat gat atc cag cca    1519
Ser Lys Val Arg Thr Leu Ser Ile Thr Asn Lys Asp Asp Ile Gln Pro
                440                 445                 450 acc cta gag caa cca gag tta tca aaa caa gac aca gaa gga aac tta    1567
Thr Leu Glu Gln Pro Glu Leu Ser Lys Gln Asp Thr Glu Gly Asn Leu
            455                 460                 465 ttg gcc cat tct cat gat ggt gga ctt ggt gac aac cat cat aat caa    1615
Leu Ala His Ser His Asp Gly Gly Leu Gly Asp Asn His His Asn Gln
        470                 475                 480 gct gca aca aat gaa atc ttt aca agt aac cct cca gct atg cct gtt    1663
Ala Ala Thr Asn Glu Ile Phe Thr Ser Asn Pro Pro Ala Met Pro Val
    485                 490                 495 gct cct gac aac aaa cag aat aac tgg tgc atg aat cca ccg cag aat    1711
Ala Pro Asp Asn Lys Gln Asn Asn Trp Cys Met Asn Pro Pro Gln Asn
500                 505                 510                 515 caa tgg ctt gtc cca gtt atg tcg cct tct gaa ggt ctt gtc tat aag    1759
Gln Trp Leu Val Pro Val Met Ser Pro Ser Glu Gly Leu Val Tyr Lys
                520                 525                 530 cct ttt gcc ggc cct tgt ccc cca gtt gga aat ctg ctg aca cca ttt    1807
Pro Phe Ala Gly Pro Cys Pro Pro Val Gly Asn Leu Leu Thr Pro Phe
            535                 540                 545 tac gcc aac tgt act ccg tta agg ctg cct tct aca cca tat ggc gtt    1855
Tyr Ala Asn Cys Thr Pro Leu Arg Leu Pro Ser Thr Pro Tyr Gly Val
        550                 555                 560 cct att cct cac cag cca cag cac atg gtc cct cct ggt gcc cct gcc    1903
Pro Ile Pro His Gln Pro Gln His Met Val Pro Pro Gly Ala Pro Ala
    565                 570                 575 atg cat atg aac tac ttc ccg cct ttc agt atg cca gtg atg aat cca    1951
Met His Met Asn Tyr Phe Pro Pro Phe Ser Met Pro Val Met Asn Pro
580                 585                 590                 595 gga aca cca gca tct gca gtg gaa caa ggg agc cat gct gct gcg cca    1999
Gly Thr Pro Ala Ser Ala Val Glu Gln Gly Ser His Ala Ala Ala Pro
                600                 605                 610 cag cct cat ggg cac atg gac cag cag tcg ctg atc tcc tgt aac atg    2047
Gln Pro His Gly His Met Asp Gln Gln Ser Leu Ile Ser Cys Asn Met
            615                 620                 625 tca cac ccg agt ggc gtt tgg agg ttt ctt gca tca agg gac agc gag    2095
Ser His Pro Ser Gly Val Trp Arg Phe Leu Ala Ser Arg Asp Ser Glu
        630                 635                 640 cca cag gcc agc agc gcc acc agc cct ttc gac agg ctc caa gtc caa    2143
Pro Gln Ala Ser Ser Ala Thr Ser Pro Phe Asp Arg Leu Gln Val Gln
    645                 650                 655 ggt gat gga agt gct ccg ttg tca ttg ttg tca ttc ttt ccc acg gct    2191
Gly Asp Gly Ser Ala Pro Leu Ser Leu Leu Ser Phe Phe Pro Thr Ala
660                 665                 670                 675 tca gct ccg aat gtc cag cct ccg ccc tca tct gga ggc tgg gac cgg    2239
Ser Ala Pro Asn Val Gln Pro Pro Pro Ser Ser Gly Gly Trp Asp Arg
                680                 685                 690 gac cag cag aac cat gta atc agg gtt gtt ccg cgt aac gcc cag act    2287
Asp Gln Gln Asn His Val Ile Arg Val Val Pro Arg Asn Ala Gln Thr
            695                 700                 705 gct tca gtc ccg aaa gcc caa cct cag ccg tca tcc gga ggc cgg gac    2335
```

```
Ala Ser Val Pro Lys Ala Gln Pro Gln Pro Ser Ser Gly Gly Arg Asp
        710                 715                 720 caa aag aac cat gta atc agg gtt gtt ccg cat aac gcg cag act gct        2383
Gln Lys Asn His Val Ile Arg Val Val Pro His Asn Ala Gln Thr Ala
725                 730                 735 tcg gag tca gca gcg tgg atc ttc cgg tca ata caa atg gag agg aac        2431
Ser Glu Ser Ala Ala Trp Ile Phe Arg Ser Ile Gln Met Glu Arg Asn
740                 745                 750                 755 caa aat gat tcg t agctggttac catatacttt cgtgtcatcc gatggcagaa          2484
Gln Asn Asp Ser aagggcgaat tc                                                          2496

<210> SEQ ID NO 2
<211> LENGTH: 2277
<212> TYPE: DNA
<213> ORGANISM: Zea mays
<220> FEATURE:
<221> NAME/KEY: CDS
<222> LOCATION: (1)...(2277)
<223> OTHER INFORMATION: ZmELF3

<400> SEQUENCE: 2 atg acg agg gga ggc ggt gga caa gga ggc aag gag gag ccg ggg aag        48
Met Thr Arg Gly Gly Gly Gly Gln Gly Gly Lys Glu Glu Pro Gly Lys
1               5                   10                  15 gtg atg ggt ccg ctg ttc ccg cgg ctc cac gtc agc gac gca ggc aag        96
Val Met Gly Pro Leu Phe Pro Arg Leu His Val Ser Asp Ala Gly Lys
                20                  25                  30 ggc ggc ggc ccg cgg gct ccg ccc agg aac aag atg gcg ctc tac gag        144
Gly Gly Gly Pro Arg Ala Pro Pro Arg Asn Lys Met Ala Leu Tyr Glu
            35                  40                  45 cag ttc acc gtg ccg tcc aac cgc ttc agc tcc ccc gcc gcc tcc gcc        192
Gln Phe Thr Val Pro Ser Asn Arg Phe Ser Ser Pro Ala Ala Ser Ala
        50                  55                  60 cgc gcc gcg ggg gcc agc ctc gtg ccc tcc acg gcg gct gcc cag gtt        240
Arg Ala Ala Gly Ala Ser Leu Val Pro Ser Thr Ala Ala Ala Gln Val
65                  70                  75                  80 tat ggt tat gac agg acg ctg ttc cag ccc ttc gat gtg cct tca aat        288
Tyr Gly Tyr Asp Arg Thr Leu Phe Gln Pro Phe Asp Val Pro Ser Asn
                85                  90                  95 gag cct cct cgt tca tct gaa aag ttc aaa gga aac act atc aac gga        336
Glu Pro Pro Arg Ser Ser Glu Lys Phe Lys Gly Asn Thr Ile Asn Gly
                100                 105                 110 cag tct aat agt aca aga aga gaa cct ttg agg atg tcc tca cag acc        384
Gln Ser Asn Ser Thr Arg Arg Glu Pro Leu Arg Met Ser Ser Gln Thr
            115                 120                 125 aag aac aag gac gtc tgt gct tca aaa tca att gcc aag tgc acc tca        432
Lys Asn Lys Asp Val Cys Ala Ser Lys Ser Ile Ala Lys Cys Thr Ser
        130                 135                 140 cag cat aga gtg ggc aac acc atc atg tct tct ggg aag aaa gtg gtc        480
Gln His Arg Val Gly Asn Thr Ile Met Ser Ser Gly Lys Lys Val Val
145                 150                 155                 160 agt gat gat gaa ttt atg gtt cct tcc atc tgt tat cct aga ttt tat        528
Ser Asp Asp Glu Phe Met Val Pro Ser Ile Cys Tyr Pro Arg Phe Tyr
                165                 170                 175 cga cag tct act caa gat cat gca gat aaa tca aaa ccc caa tct act        576
Arg Gln Ser Thr Gln Asp His Ala Asp Lys Ser Lys Pro Gln Ser Thr
                180                 185                 190 aca aac cca cac aaa agt cct gca atg tcc aaa tca tct gta gag tgc        624
Thr Asn Pro His Lys Ser Pro Ala Met Ser Lys Ser Ser Val Glu Cys
            195                 200                 205
```

-continued

```
tat agt act gtg aac aag cac ttg gac aaa atc aat gaa gct ggt agg        672
Tyr Ser Thr Val Asn Lys His Leu Asp Lys Ile Asn Glu Ala Gly Arg
210             215                 220 agg tta atg aac tct cca aag gtt aag gag aaa gaa gca gtc caa gga        720
Arg Leu Met Asn Ser Pro Lys Val Lys Glu Lys Glu Ala Val Gln Gly
225             230                 235                 240 tca aaa ggt gtg gaa gtt aaa gaa aag agt tca tca ttt cag gca tca        768
Ser Lys Gly Val Glu Val Lys Glu Lys Ser Ser Ser Phe Gln Ala Ser
            245                 250                 255 gaa aat ttc aaa gac aaa tat gct aag cta tgt caa atg agg aat aag        816
Glu Asn Phe Lys Asp Lys Tyr Ala Lys Leu Cys Gln Met Arg Asn Lys
        260                 265                 270 gca agt aat ata aat cat tgt gac aac aac ggt tgc caa cct gca agc        864
Ala Ser Asn Ile Asn His Cys Asp Asn Asn Gly Cys Gln Pro Ala Ser
    275                 280                 285 gtg aat gga aat ttc aca gaa gca aag aac cct aca gca gct aga aat        912
Val Asn Gly Asn Phe Thr Glu Ala Lys Asn Pro Thr Ala Ala Arg Asn
290                 295                 300 aca tct ttc tgt aaa cca tgt act gat gta gat agc tct aac agg aag        960
Thr Ser Phe Cys Lys Pro Cys Thr Asp Val Asp Ser Ser Asn Arg Lys
305             310                 315                 320 tct aat tta ctg gaa aga agc cca cgg gaa gtt ggt gct aag aga aaa       1008
Ser Asn Leu Leu Glu Arg Ser Pro Arg Glu Val Gly Ala Lys Arg Lys
            325                 330                 335 aga gga cat cac aat gga gag caa aat gat gat tta tct gac tcc tca       1056
Arg Gly His His Asn Gly Glu Gln Asn Asp Asp Leu Ser Asp Ser Ser
        340                 345                 350 gtg gaa tgc ata cct ggg gag gag atc tct cca gat gaa att gtt gct       1104
Val Glu Cys Ile Pro Gly Glu Glu Ile Ser Pro Asp Glu Ile Val Ala
    355                 360                 365 gct att ggt cca aag cat ttc tgg aaa gcg aga aga gct att cag aat       1152
Ala Ile Gly Pro Lys His Phe Trp Lys Ala Arg Arg Ala Ile Gln Asn
370                 375                 380 cag cag agg gtt ttt gct gtc caa gtg ttc gag ctg cat aag ctg ata       1200
Gln Gln Arg Val Phe Ala Val Gln Val Phe Glu Leu His Lys Leu Ile
385             390                 395                 400 aaa gtg cag aag tta atc gcg gca tct cca cat ctg ctt att gaa ggt       1248
Lys Val Gln Lys Leu Ile Ala Ala Ser Pro His Leu Leu Ile Glu Gly
            405                 410                 415 gat cct gtc ctt ggc aat gca tta aca gga aaa agg aac aag ctt cct       1296
Asp Pro Val Leu Gly Asn Ala Leu Thr Gly Lys Arg Asn Lys Leu Pro
        420                 425                 430 aaa gga aat tcg aaa gtt cgg acc ctg tca atc aca aac aaa gat gat       1344
Lys Gly Asn Ser Lys Val Arg Thr Leu Ser Ile Thr Asn Lys Asp Asp
    435                 440                 445 atc cag cca acc cta gag caa cca gag tta tca aaa caa gac aca gaa       1392
Ile Gln Pro Thr Leu Glu Gln Pro Glu Leu Ser Lys Gln Asp Thr Glu
450                 455                 460 gga aac tta ttg gcc cat tct cat gat ggt gga ctt ggt gac aac cat       1440
Gly Asn Leu Leu Ala His Ser His Asp Gly Gly Leu Gly Asp Asn His
465             470                 475                 480 cat aat caa gct gca aca aat gaa atc ttt aca agt aac cct cca gct       1488
His Asn Gln Ala Ala Thr Asn Glu Ile Phe Thr Ser Asn Pro Pro Ala
            485                 490                 495 atg cct gtt gct cct gac aac aaa cag aat aac tgg tgc atg aat cca       1536
Met Pro Val Ala Pro Asp Asn Lys Gln Asn Asn Trp Cys Met Asn Pro
        500                 505                 510 ccg cag aat caa tgg ctt gtc cca gtt atg tcg cct tct gaa ggt ctt       1584
Pro Gln Asn Gln Trp Leu Val Pro Val Met Ser Pro Ser Glu Gly Leu
```

-continued

```
                515                 520                 525
gtc tat aag cct ttt gcc ggc cct tgt ccc cca gtt gga aat ctg ctg    1632
Val Tyr Lys Pro Phe Ala Gly Pro Cys Pro Pro Val Gly Asn Leu Leu
    530                 535                 540 aca cca ttt tac gcc aac tgt act ccg tta agg ctg cct tct aca cca    1680
Thr Pro Phe Tyr Ala Asn Cys Thr Pro Leu Arg Leu Pro Ser Thr Pro
545                 550                 555                 560 tat ggc gtt cct att cct cac cag cca cag cac atg gtc cct cct ggt    1728
Tyr Gly Val Pro Ile Pro His Gln Pro Gln His Met Val Pro Pro Gly
                565                 570                 575 gcc cct gcc atg cat atg aac tac ttc ccg cct ttc agt atg cca gtg    1776
Ala Pro Ala Met His Met Asn Tyr Phe Pro Pro Phe Ser Met Pro Val
            580                 585                 590 atg aat cca gga aca cca gca tct gca gtg gaa caa ggg agc cat gct    1824
Met Asn Pro Gly Thr Pro Ala Ser Ala Val Glu Gln Gly Ser His Ala
        595                 600                 605 gct gcg cca cag cct cat ggg cac atg gac cag cag tcg ctg atc tcc    1872
Ala Ala Pro Gln Pro His Gly His Met Asp Gln Gln Ser Leu Ile Ser
    610                 615                 620 tgt aac atg tca cac ccg agt ggc gtt tgg agg ttt ctt gca tca agg    1920
Cys Asn Met Ser His Pro Ser Gly Val Trp Arg Phe Leu Ala Ser Arg
625                 630                 635                 640 gac agc gag cca cag gcc agc agc gcc acc agc cct ttc gac agg ctc    1968
Asp Ser Glu Pro Gln Ala Ser Ser Ala Thr Ser Pro Phe Asp Arg Leu
                645                 650                 655 caa gtc caa ggt gat gga agt gct ccg ttg tca ttg ttg tca ttc ttt    2016
Gln Val Gln Gly Asp Gly Ser Ala Pro Leu Ser Leu Leu Ser Phe Phe
            660                 665                 670 ccc acg gct tca gct ccg aat gtc cag cct ccg ccc tca tct gga ggc    2064
Pro Thr Ala Ser Ala Pro Asn Val Gln Pro Pro Pro Ser Ser Gly Gly
        675                 680                 685 tgg gac cgg gac cag cag aac cat gta atc agg gtt gtt ccg cgt aac    2112
Trp Asp Arg Asp Gln Gln Asn His Val Ile Arg Val Val Pro Arg Asn
    690                 695                 700 gcc cag act gct tca gtc ccg aaa gcc caa cct cag ccg tca tcc gga    2160
Ala Gln Thr Ala Ser Val Pro Lys Ala Gln Pro Gln Pro Ser Ser Gly
705                 710                 715                 720 ggc cgg gac caa aag aac cat gta atc agg gtt gtt ccg cat aac gcg    2208
Gly Arg Asp Gln Lys Asn His Val Ile Arg Val Val Pro His Asn Ala
                725                 730                 735 cag act gct tcg gag tca gca gcg tgg atc ttc cgg tca ata caa atg    2256
Gln Thr Ala Ser Glu Ser Ala Ala Trp Ile Phe Arg Ser Ile Gln Met
            740                 745                 750 gag agg aac caa aat gat tcg                                        2277
Glu Arg Asn Gln Asn Asp Ser
        755
```

<210> SEQ ID NO 3
<211> LENGTH: 759
<212> TYPE: PRT
<213> ORGANISM: Zea mays

<400> SEQUENCE: 3

```
Met Thr Arg Gly Gly Gly Gln Gly Gly Lys Glu Pro Gly Lys
1               5                   10                  15

Val Met Gly Pro Leu Phe Pro Arg Leu His Val Ser Asp Ala Gly Lys
            20                  25                  30

Gly Gly Gly Pro Arg Ala Pro Pro Arg Asn Lys Met Ala Leu Tyr Glu
        35                  40                  45
```

-continued

```
Gln Phe Thr Val Pro Ser Asn Arg Phe Ser Ser Pro Ala Ala Ser Ala
     50                  55                  60

Arg Ala Ala Gly Ala Ser Leu Val Pro Ser Thr Ala Ala Ala Gln Val
65                  70                  75                  80

Tyr Gly Tyr Asp Arg Thr Leu Phe Gln Pro Phe Asp Val Pro Ser Asn
                85                  90                  95

Glu Pro Pro Arg Ser Ser Glu Lys Phe Lys Gly Asn Thr Ile Asn Gly
                100                 105                 110

Gln Ser Asn Ser Thr Arg Arg Glu Pro Leu Arg Met Ser Ser Gln Thr
            115                 120                 125

Lys Asn Lys Asp Val Cys Ala Ser Lys Ser Ile Ala Lys Cys Thr Ser
    130                 135                 140

Gln His Arg Val Gly Asn Thr Ile Met Ser Ser Gly Lys Lys Val Val
145                 150                 155                 160

Ser Asp Asp Glu Phe Met Val Pro Ser Ile Cys Tyr Pro Arg Phe Tyr
                165                 170                 175

Arg Gln Ser Thr Gln Asp His Ala Asp Lys Ser Lys Pro Gln Ser Thr
                180                 185                 190

Thr Asn Pro His Lys Ser Pro Ala Met Ser Lys Ser Ser Val Glu Cys
            195                 200                 205

Tyr Ser Thr Val Asn Lys His Leu Asp Lys Ile Asn Glu Ala Gly Arg
    210                 215                 220

Arg Leu Met Asn Ser Pro Lys Val Lys Glu Lys Ala Val Gln Gly
225                 230                 235                 240

Ser Lys Gly Val Glu Val Lys Glu Lys Ser Ser Phe Gln Ala Ser
                245                 250                 255

Glu Asn Phe Lys Asp Lys Tyr Ala Lys Leu Cys Gln Met Arg Asn Lys
                260                 265                 270

Ala Ser Asn Ile Asn His Cys Asp Asn Gly Cys Gln Pro Ala Ser
    275                 280                 285

Val Asn Gly Asn Phe Thr Glu Ala Lys Asn Pro Thr Ala Ala Arg Asn
    290                 295                 300

Thr Ser Phe Cys Lys Pro Cys Thr Asp Val Asp Ser Ser Asn Arg Lys
305                 310                 315                 320

Ser Asn Leu Leu Glu Arg Ser Pro Arg Glu Val Gly Ala Lys Arg Lys
                325                 330                 335

Arg Gly His His Asn Gly Glu Gln Asn Asp Asp Leu Ser Asp Ser Ser
                340                 345                 350

Val Glu Cys Ile Pro Gly Glu Glu Ile Ser Pro Asp Glu Ile Val Ala
    355                 360                 365

Ala Ile Gly Pro Lys His Phe Trp Lys Ala Arg Arg Ala Ile Gln Asn
    370                 375                 380

Gln Gln Arg Val Phe Ala Val Gln Val Phe Glu Leu His Lys Leu Ile
385                 390                 395                 400

Lys Val Gln Lys Leu Ile Ala Ala Ser Pro His Leu Leu Ile Glu Gly
                405                 410                 415

Asp Pro Val Leu Gly Asn Ala Leu Thr Gly Lys Arg Asn Lys Leu Pro
                420                 425                 430

Lys Gly Asn Ser Lys Val Arg Thr Leu Ser Ile Thr Asn Lys Asp Asp
            435                 440                 445

Ile Gln Pro Thr Leu Glu Gln Pro Glu Leu Ser Lys Gln Asp Thr Glu
    450                 455                 460

Gly Asn Leu Leu Ala His Ser His Asp Gly Gly Leu Gly Asp Asn His
```

```
            465                 470                 475                 480
His Asn Gln Ala Ala Thr Asn Glu Ile Phe Thr Ser Asn Pro Pro Ala
                485                 490                 495
Met Pro Val Ala Pro Asp Asn Lys Gln Asn Asn Trp Cys Met Asn Pro
            500                 505                 510
Pro Gln Asn Gln Trp Leu Val Pro Val Met Ser Pro Ser Glu Gly Leu
        515                 520                 525
Val Tyr Lys Pro Phe Ala Gly Pro Cys Pro Pro Val Gly Asn Leu Leu
    530                 535                 540
Thr Pro Phe Tyr Ala Asn Cys Thr Pro Leu Arg Leu Pro Ser Thr Pro
545                 550                 555                 560
Tyr Gly Val Pro Ile Pro His Gln Pro Gln His Met Val Pro Pro Gly
                565                 570                 575
Ala Pro Ala Met His Met Asn Tyr Phe Pro Pro Phe Ser Met Pro Val
            580                 585                 590
Met Asn Pro Gly Thr Pro Ala Ser Ala Val Glu Gln Gly Ser His Ala
        595                 600                 605
Ala Ala Pro Gln Pro His Gly His Met Asp Gln Gln Ser Leu Ile Ser
    610                 615                 620
Cys Asn Met Ser His Pro Ser Gly Val Trp Arg Phe Leu Ala Ser Arg
625                 630                 635                 640
Asp Ser Glu Pro Gln Ala Ser Ser Ala Thr Ser Pro Phe Asp Arg Leu
                645                 650                 655
Gln Val Gln Gly Asp Gly Ser Ala Pro Leu Ser Leu Leu Ser Phe Phe
            660                 665                 670
Pro Thr Ala Ser Ala Pro Asn Val Gln Pro Pro Ser Ser Gly Gly
        675                 680                 685
Trp Asp Arg Asp Gln Gln Asn His Val Ile Arg Val Pro Arg Asn
    690                 695                 700
Ala Gln Thr Ala Ser Val Pro Lys Ala Gln Pro Gln Pro Ser Ser Gly
705                 710                 715                 720
Gly Arg Asp Gln Lys Asn His Val Ile Arg Val Val Pro His Asn Ala
                725                 730                 735
Gln Thr Ala Ser Glu Ser Ala Ala Trp Ile Phe Arg Ser Ile Gln Met
            740                 745                 750
Glu Arg Asn Gln Asn Asp Ser
        755

<210> SEQ ID NO 4
<211> LENGTH: 459
<212> TYPE: DNA
<213> ORGANISM: Zea mays
<220> FEATURE:
<221> NAME/KEY: promoter
<222> LOCATION: (1)...(459)
<223> OTHER INFORMATION: ZmELF3 upstream regulatory region

<400> SEQUENCE: 4 cgagggctc ctattttcgg accgtgctcg tgctggcccg aaaagtccgg cccatattcc      60
cagcactaga catgacatta ccatctgtag cagtttacct aaaatttatc taaaaacact     120 attttcact ataaacttca ctattggtaa aatagagttt aaatattggt gagtttgaag     180
ataaccttaa aaagagtaag ttgttagaac ttagaagcaa cctcaccgcc taattaacac     240
accccaaaaa aacctgcttg cacatactca accgccagcg tctccactct ccggtctccc     300
tctcatggtg gagcccacct ccgcctttgt ggatcagagc gagcattcct ttcccttccc     360
```

```
ttccctggca tcagaatcaa acgtgtcccc gcagacgctc ccaatcccat gcgcccctct    420
gctctcacgg tttgatttcc ctttcagttg ggccgccat                          459

<210> SEQ ID NO 5
<211> LENGTH: 1401
<212> TYPE: DNA
<213> ORGANISM: Arabidopsis thaliana
<220> FEATURE:
<221> NAME/KEY: CDS
<222> LOCATION: (1)...(1401)
<223> OTHER INFORMATION: bHLH041

<400> SEQUENCE: 5 atg atg cat ttg att ttg agc tgc agc tat tta ata tca atg gat gga        48
Met Met His Leu Ile Leu Ser Cys Ser Tyr Leu Ile Ser Met Asp Gly
 1               5                  10                  15 tat tac aat gaa gct tct gaa gaa cct tct tcg tct tct tct tct gga        96
Tyr Tyr Asn Glu Ala Ser Glu Glu Pro Ser Ser Ser Ser Ser Ser Gly
             20                  25                  30 agt tta gct agg agc ttg ttc cat gag tat cgc caa tcc gtt atc ccg       144
Ser Leu Ala Arg Ser Leu Phe His Glu Tyr Arg Gln Ser Val Ile Pro
         35                  40                  45 ctc caa aat ggg cat gtg cca agc atg gcg ttc atg aac aat ctt cca       192
Leu Gln Asn Gly His Val Pro Ser Met Ala Phe Met Asn Asn Leu Pro
     50                  55                  60 tac gta gaa att cga cca caa gag agt caa aga ctt gct ttt aac gac       240
Tyr Val Glu Ile Arg Pro Gln Glu Ser Gln Arg Leu Ala Phe Asn Asp
 65                  70                  75                  80 aca caa cgt ctc ttc tat cag atg aaa att gaa gca agt ctt cga gaa       288
Thr Gln Arg Leu Phe Tyr Gln Met Lys Ile Glu Ala Ser Leu Arg Glu
                 85                  90                  95 tgg ttc cct gaa gat ttc aat aga aag tct tct ccg gca aac tcc gat       336
Trp Phe Pro Glu Asp Phe Asn Arg Lys Ser Ser Pro Ala Asn Ser Asp
            100                 105                 110 tat ctc cgg cca cct cat tat ccc tct tca tcg tct tct tct ctt agt       384
Tyr Leu Arg Pro Pro His Tyr Pro Ser Ser Ser Ser Ser Ser Leu Ser
        115                 120                 125 ccc aac aac atc tcc gaa tat tcc tct ctt ttg ttc cca ctc atc cct       432
Pro Asn Asn Ile Ser Glu Tyr Ser Ser Leu Leu Phe Pro Leu Ile Pro
    130                 135                 140 aaa cct tca acg acg act gag gcc gtt aac gtt ccg gta ctt cca ccg       480
Lys Pro Ser Thr Thr Thr Glu Ala Val Asn Val Pro Val Leu Pro Pro
145                 150                 155                 160 cta gct ccg atc aat atg atc cat cca cag cat caa gag cct tta ttc       528
Leu Ala Pro Ile Asn Met Ile His Pro Gln His Gln Glu Pro Leu Phe
                165                 170                 175 cgt aac cgt caa cgt gag gaa gaa gca atg acg caa gca atc tta gcg       576
Arg Asn Arg Gln Arg Glu Glu Glu Ala Met Thr Gln Ala Ile Leu Ala
            180                 185                 190 gtt tta acg ggg cca tca agt cct ccg tca act tct tcc tcg ccg cag       624
Val Leu Thr Gly Pro Ser Ser Pro Pro Ser Thr Ser Ser Ser Pro Gln
        195                 200                 205 cgt aaa gga aga gcc acc gct ttt aag aga tat tac tcc atg att agt       672
Arg Lys Gly Arg Ala Thr Ala Phe Lys Arg Tyr Tyr Ser Met Ile Ser
    210                 215                 220 gac cgc ggt aga gcc ccg ctt ccg agt gtt cgg aag caa agt atg atg       720
Asp Arg Gly Arg Ala Pro Leu Pro Ser Val Arg Lys Gln Ser Met Met
225                 230                 235                 240 aca aga gcg atg tcc ttc tac aat agg ctt aac att aac cag aga gag       768
Thr Arg Ala Met Ser Phe Tyr Asn Arg Leu Asn Ile Asn Gln Arg Glu
```

-continued

```
                       245                 250                 255
cgt ttt act agg gaa aac gct act aca cac ggc gag gga agc ggt gga      816
Arg Phe Thr Arg Glu Asn Ala Thr Thr His Gly Glu Gly Ser Gly Gly
            260                 265                 270 agt gga ggg ggt gga cgt tat act agc ggg cca agc gca acg caa ctg      864
Ser Gly Gly Gly Gly Arg Tyr Thr Ser Gly Pro Ser Ala Thr Gln Leu
            275                 280                 285 caa cat atg ata tcg gag agg aaa cgg cga gag aag ctt aat gag agc      912
Gln His Met Ile Ser Glu Arg Lys Arg Arg Glu Lys Leu Asn Glu Ser
            290                 295                 300 ttt caa gca ttg aga tct ctc ctt cct ccc gga act aag aaa gat aaa      960
Phe Gln Ala Leu Arg Ser Leu Leu Pro Pro Gly Thr Lys Lys Asp Lys
305                 310                 315                 320 gca tcg gtc ctc tcc att gca aga gag caa cta tct tct ttg caa ggt     1008
Ala Ser Val Leu Ser Ile Ala Arg Glu Gln Leu Ser Ser Leu Gln Gly
            325                 330                 335 gag att tcg aaa cta cta gag aga aat cgg gag gta gag gca aag cta     1056
Glu Ile Ser Lys Leu Leu Glu Arg Asn Arg Glu Val Glu Ala Lys Leu
            340                 345                 350 gca gga gaa aga gag att gaa aat gat tta cga ccc gaa gag agg ttt     1104
Ala Gly Glu Arg Glu Ile Glu Asn Asp Leu Arg Pro Glu Glu Arg Phe
            355                 360                 365 aac gtt cgt ata aga cat ata cct gaa tca aca tct aga gag agg act     1152
Asn Val Arg Ile Arg His Ile Pro Glu Ser Thr Ser Arg Glu Arg Thr
            370                 375                 380 ttg gat cta cga gtt gtt cta agg gga gac atc att agg gtt gat gat     1200
Leu Asp Leu Arg Val Val Leu Arg Gly Asp Ile Ile Arg Val Asp Asp
385                 390                 395                 400 ttg atg ata aga ctt ctc gaa ttc ttg aag caa atc aac aat gtg agc     1248
Leu Met Ile Arg Leu Leu Glu Phe Leu Lys Gln Ile Asn Asn Val Ser
            405                 410                 415 tta gtg tca atc gaa gct cga act cta gct aga gca gag ggg gat act     1296
Leu Val Ser Ile Glu Ala Arg Thr Leu Ala Arg Ala Glu Gly Asp Thr
            420                 425                 430 tca att gtt ctt gtg atc agc tta agg ctc aag att gag ggt gaa tgg     1344
Ser Ile Val Leu Val Ile Ser Leu Arg Leu Lys Ile Glu Gly Glu Trp
            435                 440                 445 gac gaa tca gcc ttc caa gaa gca gtc aga agg gtt gtt gct gac ttg     1392
Asp Glu Ser Ala Phe Gln Glu Ala Val Arg Arg Val Val Ala Asp Leu
450                 455                 460 gct cac tga                                                         1401
Ala His *
465
```

<210> SEQ ID NO 6
<211> LENGTH: 466
<212> TYPE: PRT
<213> ORGANISM: Arabidopsis thaliana
<220> FEATURE:
<221> NAME/KEY: DOMAIN
<222> LOCATION: (287)...(339)
<223> OTHER INFORMATION: bHLH domain

<400> SEQUENCE: 6

```
Met Met His Leu Ile Leu Ser Cys Ser Tyr Leu Ile Ser Met Asp Gly
1               5                   10                  15

Tyr Tyr Asn Glu Ala Ser Glu Glu Pro Ser Ser Ser Ser Ser Ser Gly
            20                  25                  30

Ser Leu Ala Arg Ser Leu Phe His Glu Tyr Arg Gln Ser Val Ile Pro
        35                  40                  45
```

-continued

```
Leu Gln Asn Gly His Val Pro Ser Met Ala Phe Met Asn Asn Leu Pro
     50                  55                  60
Tyr Val Glu Ile Arg Pro Gln Glu Ser Gln Arg Leu Ala Phe Asn Asp
 65                  70                  75                  80
Thr Gln Arg Leu Phe Tyr Gln Met Lys Ile Glu Ala Ser Leu Arg Glu
                 85                  90                  95
Trp Phe Pro Glu Asp Phe Asn Arg Lys Ser Ser Pro Ala Asn Ser Asp
                100                 105                 110
Tyr Leu Arg Pro Pro His Tyr Pro Ser Ser Ser Ser Ser Leu Ser
            115                 120                 125
Pro Asn Asn Ile Ser Glu Tyr Ser Ser Leu Leu Phe Pro Leu Ile Pro
    130                 135                 140
Lys Pro Ser Thr Thr Thr Glu Ala Val Asn Val Pro Val Leu Pro Pro
145                 150                 155                 160
Leu Ala Pro Ile Asn Met Ile His Pro Gln His Gln Glu Pro Leu Phe
                165                 170                 175
Arg Asn Arg Gln Arg Glu Glu Glu Ala Met Thr Gln Ala Ile Leu Ala
            180                 185                 190
Val Leu Thr Gly Pro Ser Ser Pro Pro Ser Thr Ser Ser Pro Gln
        195                 200                 205
Arg Lys Gly Arg Ala Thr Ala Phe Lys Arg Tyr Tyr Ser Met Ile Ser
    210                 215                 220
Asp Arg Gly Arg Ala Pro Leu Pro Ser Val Arg Lys Gln Ser Met Met
225                 230                 235                 240
Thr Arg Ala Met Ser Phe Tyr Asn Arg Leu Asn Ile Asn Gln Arg Glu
                245                 250                 255
Arg Phe Thr Arg Glu Asn Ala Thr Thr His Gly Glu Gly Ser Gly Gly
            260                 265                 270
Ser Gly Gly Gly Gly Arg Tyr Thr Ser Gly Pro Ser Ala Thr Gln Leu
        275                 280                 285
Gln His Met Ile Ser Glu Arg Lys Arg Arg Glu Lys Leu Asn Glu Ser
    290                 295                 300
Phe Gln Ala Leu Arg Ser Leu Leu Pro Pro Gly Thr Lys Lys Asp Lys
305                 310                 315                 320
Ala Ser Val Leu Ser Ile Ala Arg Glu Gln Leu Ser Ser Leu Gln Gly
                325                 330                 335
Glu Ile Ser Lys Leu Leu Glu Arg Asn Arg Glu Val Glu Ala Lys Leu
            340                 345                 350
Ala Gly Glu Arg Glu Ile Glu Asn Asp Leu Arg Pro Glu Glu Arg Phe
        355                 360                 365
Asn Val Arg Ile Arg His Ile Pro Glu Ser Thr Ser Arg Glu Arg Thr
    370                 375                 380
Leu Asp Leu Arg Val Val Leu Arg Gly Asp Ile Ile Arg Val Asp Asp
385                 390                 395                 400
Leu Met Ile Arg Leu Leu Glu Phe Leu Lys Gln Ile Asn Asn Val Ser
                405                 410                 415
Leu Val Ser Ile Glu Ala Arg Thr Leu Ala Arg Ala Glu Gly Asp Thr
            420                 425                 430
Ser Ile Val Leu Val Ile Ser Leu Arg Leu Lys Ile Glu Gly Glu Trp
        435                 440                 445
Asp Glu Ser Ala Phe Gln Glu Ala Val Arg Arg Val Val Ala Asp Leu
    450                 455                 460
Ala His
```

465

```
<210> SEQ ID NO 7
<211> LENGTH: 695
<212> TYPE: PRT
<213> ORGANISM: Arabidopsis thaliana

<400> SEQUENCE: 7
```

| | | | | | | | | | | | | | | |
|---|---|---|---|---|---|---|---|---|---|---|---|---|---|---|
| Met | Lys | Arg | Gly | Lys | Asp | Glu | Glu | Lys | Ile | Leu | Glu | Pro | Met | Phe | Pro |
| 1 | | | | 5 | | | | | 10 | | | | | 15 | |
| Arg | Leu | His | Val | Asn | Asp | Ala | Asp | Lys | Gly | Gly | Pro | Arg | Ala | Pro | Pro |
| | | | 20 | | | | | 25 | | | | | 30 | | |
| Arg | Asn | Lys | Met | Ala | Leu | Tyr | Glu | Gln | Leu | Ser | Ile | Pro | Ser | Gln | Arg |
| | | 35 | | | | | 40 | | | | | 45 | | | |
| Phe | Gly | Asp | His | Gly | Thr | Met | Asn | Ser | Arg | Ser | Asn | Asn | Thr | Ser | Thr |
| | 50 | | | | | 55 | | | | | 60 | | | | |
| Leu | Val | His | Pro | Gly | Pro | Ser | Ser | Gln | Pro | Cys | Gly | Val | Glu | Arg | Asn |
| 65 | | | | | 70 | | | | | 75 | | | | | 80 |
| Leu | Ser | Val | Gln | His | Leu | Asp | Ser | Ser | Ala | Ala | Asn | Gln | Ala | Thr | Glu |
| | | | | 85 | | | | | 90 | | | | | 95 | |
| Lys | Phe | Val | Ser | Gln | Met | Ser | Phe | Met | Glu | Asn | Val | Arg | Ser | Ser | Ala |
| | | | 100 | | | | | 105 | | | | | 110 | | |
| Gln | His | Asp | Gln | Arg | Lys | Met | Val | Arg | Glu | Glu | Asp | Phe | Ala | Val |
| | | 115 | | | | | 120 | | | | | 125 | | | |
| Pro | Val | Tyr | Ile | Asn | Ser | Arg | Arg | Ser | Gln | Ser | His | Gly | Arg | Thr | Lys |
| | 130 | | | | | 135 | | | | | 140 | | | | |
| Ser | Gly | Ile | Glu | Lys | Glu | Lys | His | Thr | Pro | Met | Val | Ala | Pro | Ser | Ser |
| 145 | | | | | 150 | | | | | 155 | | | | | 160 |
| His | His | Ser | Ile | Arg | Phe | Gln | Glu | Val | Asn | Gln | Thr | Gly | Ser | Lys | Gln |
| | | | | 165 | | | | | 170 | | | | | 175 | |
| Asn | Val | Cys | Leu | Ala | Thr | Cys | Ser | Lys | Pro | Glu | Val | Arg | Asp | Gln | Val |
| | | | 180 | | | | | 185 | | | | | 190 | | |
| Lys | Ala | Asn | Ala | Arg | Ser | Gly | Gly | Phe | Val | Ile | Ser | Leu | Asp | Val | Ser |
| | | 195 | | | | | 200 | | | | | 205 | | | |
| Val | Thr | Glu | Glu | Ile | Asp | Leu | Glu | Lys | Ser | Ala | Ser | Ser | His | Asp | Arg |
| | 210 | | | | | 215 | | | | | 220 | | | | |
| Val | Asn | Asp | Tyr | Asn | Ala | Ser | Leu | Arg | Gln | Glu | Ser | Arg | Asn | Arg | Leu |
| 225 | | | | | 230 | | | | | 235 | | | | | 240 |
| Tyr | Arg | Asp | Gly | Gly | Lys | Thr | Arg | Leu | Lys | Asp | Thr | Asp | Asn | Gly | Ala |
| | | | | 245 | | | | | 250 | | | | | 255 | |
| Glu | Ser | His | Leu | Ala | Thr | Glu | Asn | His | Ser | Gln | Glu | Gly | His | Gly | Ser |
| | | | 260 | | | | | 265 | | | | | 270 | | |
| Pro | Glu | Asp | Ile | Asp | Asn | Asp | Arg | Glu | Tyr | Ser | Lys | Ser | Arg | Ala | Cys |
| | | 275 | | | | | 280 | | | | | 285 | | | |
| Ala | Ser | Leu | Gln | Gln | Ile | Asn | Glu | Glu | Ala | Ser | Asp | Val | Ser | Asp |
| | 290 | | | | | 295 | | | | | 300 | | | | |
| Asp | Ser | Met | Val | Asp | Ser | Ile | Ser | Ser | Ile | Asp | Val | Ser | Pro | Asp | Asp |
| 305 | | | | | 310 | | | | | 315 | | | | | 320 |
| Val | Val | Gly | Ile | Leu | Gly | Gln | Lys | Arg | Phe | Trp | Arg | Ala | Arg | Lys | Ala |
| | | | | 325 | | | | | 330 | | | | | 335 | |
| Ile | Ala | Asn | Gln | Gln | Arg | Val | Phe | Ala | Val | Gln | Leu | Phe | Glu | Leu | His |
| | | | 340 | | | | | 345 | | | | | 350 | | |
| Arg | Leu | Ile | Lys | Val | Gln | Lys | Leu | Ile | Ala | Ala | Ser | Pro | Asp | Leu | Leu |
| | | 355 | | | | | 360 | | | | | 365 | | | |

```
Leu Asp Glu Ile Ser Phe Leu Gly Lys Val Ser Ala Lys Ser Tyr Pro
    370                 375                 380

Val Lys Lys Leu Leu Pro Ser Glu Phe Leu Val Lys Pro Pro Leu Pro
385                 390                 395                 400

His Val Val Val Lys Gln Arg Gly Asp Ser Glu Lys Thr Asp Gln His
                405                 410                 415

Lys Met Glu Ser Ser Ala Glu Asn Val Val Gly Arg Leu Ser Asn Gln
            420                 425                 430

Gly His His Gln Gln Ser Asn Tyr Met Pro Phe Ala Asn Asn Pro Pro
        435                 440                 445

Ala Ser Pro Ala Pro Asn Gly Tyr Cys Phe Pro Gln Pro Pro Pro
    450                 455                 460

Ser Gly Asn His Gln Gln Trp Leu Ile Pro Val Met Ser Pro Ser Glu
465                 470                 475                 480

Gly Leu Ile Tyr Lys Pro His Pro Gly Met Ala His Thr Gly His Tyr
                485                 490                 495

Gly Gly Tyr Tyr Gly His Tyr Met Pro Thr Pro Met Val Met Pro Gln
            500                 505                 510

Tyr His Pro Gly Met Gly Phe Pro Pro Gly Asn Gly Tyr Phe Pro
    515                 520                 525

Pro Tyr Gly Met Met Pro Thr Ile Met Asn Pro Tyr Cys Ser Ser Gln
530                 535                 540

Gln Gln Gln Gln Gln Gln Pro Asn Glu Gln Met Asn Gln Phe Gly His
545                 550                 555                 560

Pro Gly Asn Leu Gln Asn Thr Gln Gln Gln Gln Arg Ser Asp Asn
                565                 570                 575

Glu Pro Ala Pro Gln Gln Gln Gln Pro Thr Lys Ser Tyr Pro Arg
    580                 585                 590

Ala Arg Lys Ser Arg Gln Gly Ser Thr Gly Ser Ser Pro Ser Gly Pro
                595                 600                 605

Gln Gly Ile Ser Gly Ser Lys Ser Phe Arg Pro Phe Ala Ala Val Asp
    610                 615                 620

Glu Asp Ser Asn Ile Asn Asn Ala Pro Glu Gln Thr Met Thr Thr Thr
625                 630                 635                 640

Thr Thr Thr Thr Arg Thr Thr Val Thr Gln Thr Thr Arg Asp Gly Gly
                645                 650                 655

Gly Val Thr Arg Val Ile Lys Val Val Pro His Asn Ala Lys Leu Ala
            660                 665                 670

Ser Glu Asn Ala Ala Arg Ile Phe Gln Ser Ile Gln Glu Arg Lys
        675                 680                 685

Arg Tyr Asp Ser Ser Lys Pro
    690                 695

<210> SEQ ID NO 8
<211> LENGTH: 760
<212> TYPE: PRT
<213> ORGANISM: Oryza sativa

<400> SEQUENCE: 8

Met Ala Thr Arg Gly Gly Gly Gly Gly Gly Lys Glu Ala Lys
1               5                   10                  15

Gly Lys Val Met Gly Pro Leu Phe Pro Arg Leu His Val Asn Asp Ala
                20                  25                  30

Ala Lys Gly Gly Gly Pro Arg Ala Pro Pro Arg Asn Lys Met Ala Leu
            35                  40                  45
```

-continued

```
Tyr Glu Gln Phe Thr Val Pro Ser His Arg Phe Ser Gly Gly Gly
     50                  55                  60
Gly Gly Gly Val Gly Gly Ser Pro Ala His Ser Thr Ser Ala Ala Ser
 65                  70                  75                  80
Gln Ser Gln Ser Gln Ser Gln Val Tyr Gly Arg Asp Ser Ser Leu Phe
                     85                  90                  95
Gln Pro Phe Asn Val Pro Ser Asn Arg Pro Gly His Ser Thr Glu Lys
                100                 105                 110
Ile Asn Ser Asp Lys Ile Asn Lys Lys Ile Ser Gly Ser Arg Lys Glu
                115                 120                 125
Leu Gly Met Leu Ser Ser Gln Thr Lys Gly Met Asp Ile Tyr Ala Ser
130                 135                 140
Arg Ser Thr Ala Glu Ala Pro Gln Arg Arg Ala Glu Asn Thr Ile Lys
145                 150                 155                 160
Ser Ser Ser Gly Lys Arg Leu Ala Asp Asp Asp Glu Phe Met Val Pro
                165                 170                 175
Ser Val Phe Asn Ser Arg Phe Pro Gln Tyr Ser Thr Gln Glu Asn Ala
                180                 185                 190
Gly Val Gln Asp Gln Ser Thr Pro Leu Val Ala Ala Asn Pro His Lys
                195                 200                 205
Ser Pro Ser Thr Val Ser Lys Ser Ser Thr Lys Cys Tyr Asn Thr Val
210                 215                 220
Ser Lys Lys Leu Glu Arg Ile His Val Ser Asp Val Lys Ser Arg Thr
225                 230                 235                 240
Pro Leu Lys Asp Lys Glu Met Glu Ala Ala Gln Thr Ser Lys Asn Val
                245                 250                 255
Glu Val Glu Lys Ser Ser Ser Phe His Ala Ser Lys Asp Met Phe Glu
                260                 265                 270
Ser Arg His Ala Lys Val Tyr Pro Lys Met Asp Lys Thr Gly Ile Ile
                275                 280                 285
Asn Asp Ser Asp Glu Pro His Gly Gly Asn Ser Gly His Gln Ala Thr
290                 295                 300
Ser Arg Asn Gly Gly Ser Met Lys Phe Gln Asn Pro Pro Met Arg Arg
305                 310                 315                 320
Asn Glu Ile Ser Ser Asn Pro Ser Ser Glu Asn Thr Asp Arg His Tyr
                325                 330                 335
Asn Leu Pro Gln Gly Gly Ile Glu Glu Thr Gly Thr Lys Arg Lys Arg
                340                 345                 350
Leu Leu Glu Gln His Asp Ala Glu Lys Ser Asp Asp Val Ser Arg Leu
                355                 360                 365
Leu Glu Gln His Asp Ala Glu Asn Ile Asp Asp Val Ser Asp Ser Ser
                370                 375                 380
Val Glu Cys Ile Thr Gly Trp Glu Ile Ser Pro Asp Lys Ile Val Gly
385                 390                 395                 400
Ala Ile Gly Thr Lys His Phe Trp Lys Ala Arg Arg Ala Ile Met Asn
                405                 410                 415
Gln Gln Arg Val Phe Ala Val Gln Val Phe Glu Leu His Lys Leu Val
                420                 425                 430
Lys Val Gln Lys Leu Ile Ala Ala Ser Pro His Val Leu Ile Glu Ser
                435                 440                 445
Asp Pro Cys Leu Gly Asn Ala Leu Leu Gly Ser Lys Asn Lys Leu Val
450                 455                 460
```

-continued

```
Glu Glu Asn Leu Lys Ala Gln Pro Leu Leu Val Ala Thr Ile Asp Asp
465                 470                 475                 480

Val Glu Pro Ser Leu Gln Gln Pro Glu Val Ser Lys Glu Asn Thr Glu
            485                 490                 495

Asp Ser Pro Pro Ser Pro His Asp Thr Gly Leu Gly Ser Gly Gln Arg
        500                 505                 510

Asp Gln Ala Ala Thr Asn Gly Val Ser Lys Ser Asn Arg Arg Ala Thr
    515                 520                 525

Pro Val Ala Ser Asp Asn Lys Gln Asn Asn Trp Gly Val Gln Leu Gln
530                 535                 540

Pro Pro Gln Asn Gln Trp Leu Val Pro Val Met Ser Pro Leu Glu Gly
545                 550                 555                 560

Leu Val Tyr Lys Pro Tyr Ser Gly Pro Cys Pro Pro Ala Gly Ser Ile
            565                 570                 575

Leu Ala Pro Phe Tyr Ala Asn Cys Thr Pro Leu Ser Leu Pro Ser Thr
        580                 585                 590

Ala Gly Asp Phe Met Asn Ser Ala Tyr Gly Val Pro Met Pro His Gln
    595                 600                 605

Pro Gln His Met Gly Ala Pro Gly Pro Ser Met Pro Met Asn Tyr
610                 615                 620

Phe Pro Pro Phe Ser Ile Pro Val Met Asn Pro Thr Ala Pro Ala Pro
625                 630                 635                 640

Val Val Glu Gln Gly Arg His Pro Ser Met Pro Gln Pro Tyr Gly Asn
            645                 650                 655

Phe Glu Gln Gln Ser Trp Ile Ser Cys Asn Met Ser His Pro Ser Gly
        660                 665                 670

Ile Trp Arg Phe His Ala Ser Arg Asp Ser Glu Ala Gln Ala Ser Ser
    675                 680                 685

Ala Ser Ser Pro Phe Asp Arg Phe Gln Cys Ser Gly Ser Gly Pro Val
690                 695                 700

Ser Ala Phe Pro Thr Val Ser Ala Gln Asn Asn Gln Pro Gln Pro Ser
705                 710                 715                 720

Tyr Ser Ser Arg Asp Asn Gln Thr Asn Val Ile Lys Val Val Pro His
            725                 730                 735

Asn Ser Arg Thr Ala Ser Glu Ser Ala Ala Arg Ile Phe Arg Ser Ile
        740                 745                 750

Gln Met Glu Arg Gln Arg Asp Asp
    755                 760

<210> SEQ ID NO 9
<211> LENGTH: 20
<212> TYPE: DNA
<213> ORGANISM: Arabidopsis thaliana
<220> FEATURE:
<221> NAME/KEY: misc_signal
<222> LOCATION: (0)...(0)
<223> OTHER INFORMATION: evening element

<400> SEQUENCE: 9
gtcccgtcaa aatatctcgc                                              20

<210> SEQ ID NO 10
<211> LENGTH: 473
<212> TYPE: PRT
<213> ORGANISM: Artificial Sequence
<220> FEATURE:
<223> OTHER INFORMATION: Consensus
```

<400> SEQUENCE: 10

```
Gly Gly Lys Glu Asp Gly Lys Val Met Gly Pro Leu Phe Pro Arg Leu
  1               5                  10                  15
His Val Asn Asp Ala Ala Lys Gly Gly Gly Pro Arg Ala Pro Pro Arg
             20                  25                  30
Asn Lys Met Ala Leu Tyr Glu Gln Phe Thr Val Pro Ser Asn Arg Phe
             35                  40                  45
Ser Gly Ala Ala Ala Gly Thr Ser Ser Leu Val Ser Ala Ala Ser Gln
 50                  55                  60
Val Tyr Gly Asp Arg Ser Leu Phe Gln Pro Phe Val Pro Ser Asn Pro
 65                  70                  75                  80
Ser Ser Glu Lys Ile Asn Ser Arg Lys Glu Leu Ser Ser Gln Thr Lys
             85                  90                  95
Asp Ile Ala Ser Lys Ser Ile Ala Ser Gln Arg Val Asn Thr Ile Ser
            100                 105                 110
Ser Gly Lys Lys Val Asp Asp Glu Phe Met Val Pro Ser Ile Asn
            115                 120                 125
Ser Arg Phe Gln Ser Thr Gln Asp Ala Gly Ile Asp Lys Ser Thr Pro
            130                 135                 140
Leu Val Ala Asn Pro His Lys Ser Pro Met Ser Lys Ser Ser Thr Cys
145                 150                 155                 160
Tyr Asn Thr Val Lys Leu Asp Lys Ile Glu Ala Lys Leu Lys Lys Lys
                165                 170                 175
Glu Glu Ala Gln Ser Lys Val Glu Val Glu Ser Ser Asp Phe Asp
            180                 185                 190
Lys His Ala Leu Gln Lys Tyr Ile Asn His Asn Gly Gln Ser Asn Gly
            195                 200                 205
Ala Ser Asn Pro Ala Arg Asn Ser Pro Ser Asp Asp Ser Arg Lys Ser
            210                 215                 220
Asn Leu Glu Gly Lys Arg Lys Leu Leu Ile Asp Asp Ile Pro Ser Leu
225                 230                 235                 240
Gln Pro Glu Leu Ser Lys Glu Asn Thr Glu Gly Leu Ala His Asp Gly
                245                 250                 255
Leu Gly His Gln Ala Ala Thr Asn Ile Phe Ser Asn Pro Ala Ser
            260                 265                 270
Pro Val Ala Asp Asn Lys Gln Asn Asn Trp Met Asn Pro Gln Asn Gln
            275                 280                 285
Trp Leu Val Pro Val Met Ser Pro Ser Glu Gly Leu Val Tyr Lys Pro
            290                 295                 300
His Ala Gly Pro Cys Pro Pro Ala Gly Ile Leu Pro Phe Tyr Ala Asn
305                 310                 315                 320
Cys Thr Pro Leu Leu Pro Ser Thr Tyr Gly Val Pro Ile Pro His Gln
                325                 330                 335
Pro Gln His Met Pro Pro Gly Pro Ala Met Met Asn Tyr Phe Pro Pro
            340                 345                 350
Phe Ser Met Pro Val Met Asn Pro Pro Ala Val Glu Gln Gly His Ala
            355                 360                 365
Pro Gln Pro His Gly Asn Met Asp Gln Gln Ser Ile Ser Cys Asn Met
            370                 375                 380
Ser His Pro Ser Gly Ile Trp Arg Phe Ala Ser Arg Asp Ser Glu Gln
385                 390                 395                 400
Ala Ser Ser Ala Thr Ser Pro Phe Asp Arg Gln Ser Gly Gly Ser Ser
                405                 410                 415
```

```
Pro Leu Ser Phe Pro Thr Ala Ser Ala Asn Gln Pro Ala Asn Asn Thr
            420                 425                 430

Ser Lys Gln Pro Ser Ser Arg Asp Asn Thr Val Ile Lys Val Val Pro
        435                 440                 445

His Asn Ala Lys Thr Ala Ser Glu Ser Ala Ala Arg Ile Phe Arg Ser
    450                 455                 460

Ile Gln Met Glu Arg Asn Arg Asp Ser
465                 470
```

US 7,868,224 B2

COMPOSITIONS AND METHODS FOR INCREASING PLANT TOLERANCE TO HIGH POPULATION DENSITY

CROSS REFERENCE

This utility application claims the benefit U.S. Provisional Application No. 60/779,720, filed Mar. 7, 2006, which is incorporated herein by reference.

FIELD OF THE INVENTION

The present invention is drawn to the genetic manipulation of plants, particularly to manipulating plants to increase tolerance to high population density.

BACKGROUND OF THE INVENTION

Light plays a vital role in plant growth and development. Plants perceive light in the environment using a number of photoreceptor systems that control developmental processes such as germination, photomorphogenesis, flowering, and senescence, as well as metabolic processes such as photosynthesis. Plant cells not only obtain energy and chemical disturbance from photons, they also obtain information. The excitation of chlorophyll molecules by visible light provides the energy for $CO_2$ reduction and for maintenance of metabolic activities.

In environments with high primary productivity, the single most important determinant of the light climate experienced by a plant is most often its neighbors. Plants acclimate morphologically and biochemically to the light environment of their neighborhood. They forage for light in the three-dimensional canopy space using a battery of informational photoreceptors. Phytochromes represent a family of red-light-absorbing photoreceptors that can exist in the physiologically inactive Pr form and the active Pfr form. Pr and Pfr are interconvertible by red or far-red (FR) light, respectively. This absorption profile is extremely useful for the detection of shade or the presence of neighboring plants. At high proportions of FR radiation under shade conditions or in dense plant populations, the photoequilibrium is shifted toward the inactive Pr form. Under these conditions, green plants exhibit various symptoms of the shade-avoidance response, such as promotion of stem and petiole elongation, reduced leaf thickness, reduced chlorophyll synthesis, and increased apical dominance. The shade-avoidance response reduces the availability of resources for storage and reproduction.

The ability of plants to adjust their morphology in response to crowding is almost certainly a key element to success for the individual plant in environments of high primary productivity. Increases in yield over the last several decades have been attributed largely to increased density tolerance. Transgenic strategies will be required to further increase the productivity of plants beyond what is possible with conventional breeding. Thus, genes and methods for improving the plant response to density planting are needed.

SUMMARY OF THE INVENTION

Compositions and methods for suppressing the shade-avoidance response of plants and improving plant growth and yield are provided. In particular, the compositions and methods of the invention alter the plant response to light quality and increase the plant tolerance to conditions of limited light, including that caused by high population density. Compositions of the invention include an early flowering 3 (ELF3) maize gene as well as an *Arabidopsis* basic helix-loop-helix transcription factor (bHLH-041), and fragments and variants thereof. The bHLH-041 is a member of a class of transcription factors involved in a large number of plant responses, including some members that directly interact with phytochromes involved in light perception. The methods of the invention involve manipulating expression of the ELF3 and bHLH-041 genes to alter the response of a plant to light quality and suppress the high-density-invoked survival mode of development. Particularly, the methods involve expression or over-expression of the ELF3 gene in plants and downregulation of the bHLH-041 gene or gene coding for a similar transcription factor to suppress the shade-avoidance response. Plants so modified will tolerate conditions of low light, such as those that occur indoors, in shady landscapes, and in conditions of high population density. In crop situations the modification will result in higher yields under high plant density, relative to a control plant. The polynucleotides of the invention can be used alone, in combination, or with other genes and mechanisms for increasing plant yield. The invention provides methods for growing crop plants at high population densities for yield enhancement.

Additionally, a promoter sequence is provided. The maize ELF3 promoter sequence is useful for driving expression of polynucleotides of interest in a plant.

BRIEF DESCRIPTION OF THE DRAWINGS

FIG. 1 shows an alignment of the maize ELF3 protein sequence (SEQ ID NO: 3) with the *Arabidopsis thaliana* ELF3 sequence (At2g25930; GenBank Accession No. NM_128153; SEQ ID NO: 7) and the *Oryza sativa* ELF3 sequence (GenBank Accession No. BAA83571; SEQ ID NO: 8). Conserved residues are indicated in the consensus sequence (SEQ ID NO: 10).

FIG. 3A shows elements within the ZM-ELF3 promoter that resemble the "evening element" present in a number of circadian clock associated genes. Nucleotide positions are relative to the nucleotide sequence set forth in SEQ ID NO: 4. The *Arabidopsis thaliana* evening element (SEQ ID NO: 9) is shown for comparison. FIG. 3B shows the upstream sequence of the ZM-ELF3 gene with putative evening elements underlined in bold. A putative CAAT box is italicized, and the transcription start site is italicized and double underlined. Nucleotides 1-459 are shown in SEQ ID NO: 4; nucleotides 460-625 correspond to nucleotides 1-166 of SEQ ID NO: 1.

FIG. 4 shows effects of plant density in *Arabidopsis*. Wild-type (Columbia) plants were grown under a range of densities (1: one plant in 4 $cm^2$; 2: one plant in 3 $cm^2$; 3 one plant in 2 $cm^2$; 4: one plant in 1 $cm^2$). Overall bolt height in cm at flowering (panel A), number of bolts at flowering (B), longest leaf length (C) and silique length (D).

FIG. 5 shows the effect of density on flowering time in *Arabidopsis*. Increasing density from left to right decreases time to flowering and size of plant at flowering. Ten plants were measured from each treatment.

FIG. 6 describes activation tagging of the ELF3 mutant. Panel A provides a map of the genomic sequence surrounding ELF3 and shows the location of the 35S activation tag. Panel B shows analysis of three positive and one negative plant demonstrating over-expression of ELF3 in the activation tagged lines (144-1 to 3). Panel C shows a PstI-digested Southern blot of DNA isolated from three ELF3 activation tagged lines, indicating that a single T-DNA copy is present.

FIG. 7 shows the effect of density on activation-tagged lines in an interplanting experiment. Activation-tagged lines 50-1 (bHLH-041 protein) and 144-1 (ELF3) have different responses to high plant density as indicated by leaf length (upper panel) and bolt height (lower panel). Activation-tagged seeds were interplanted with wild-type plants at the second highest density (one plant in 2 cm$^2$) and measured at mid-flowering (stage 6.5). Interplanting involved seeding experimental plants amongst control plants where every fifth plant was experimental.

DETAILED DESCRIPTION OF THE INVENTION

Figure 2A:
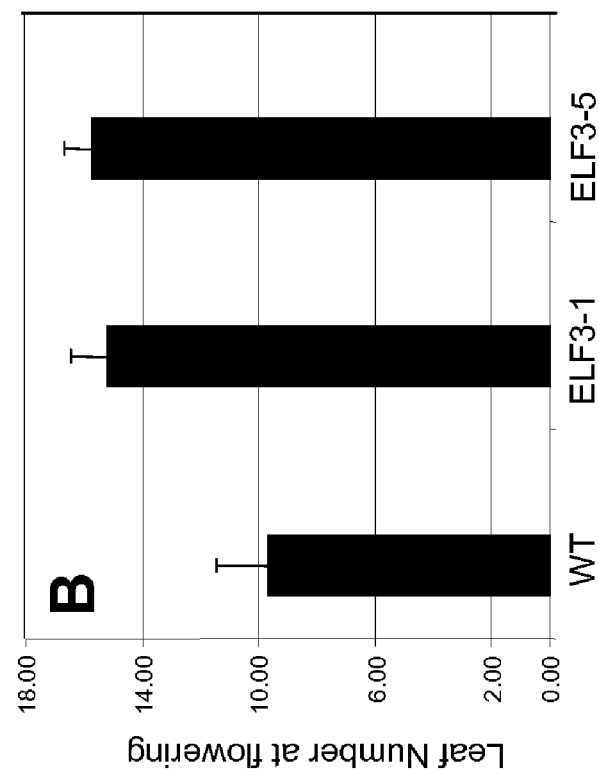
FIGS. 2A and 2B show the effects of over-expression of ZM-ELF3 on leaf length (FIG. 2A) and leaf number at flowering (FIG. 2B) in transgenic *Arabidopsis* grown at high density.

Compositions and methods for increasing yield in a plant or crop are provided. In particular, the compositions and methods of the invention suppress the shade-avoidance response of the plant by altering the plant response to light quality and increasing the plant tolerance to density. In this manner, the plant can be grown in a high density setting without sacrificing yield, thus increasing the overall yield of the crop. Compositions of the invention include the early flowering 3 (ELF3) promoter and coding sequence from maize, the coding sequence for a basic helix-loop-helix transcription factor (bHLH-041) from *Arabidopsis*, and variants and fragments thereof, as well as polynucleotides and constructs for suppression of expression of the bHLH-041 gene and genes for similar transcription factors in plants. The coding sequence for the maize ELF3 gene is set forth as nucleotides 167 through 2444 of SEQ ID NO: 1 and as SEQ ID NO: 2, and the amino acid sequence for the encoded ELF3 polypeptide is set forth in SEQ ID NO: 3. The ELF3 promoter sequence is set forth in SEQ ID NO: 4. The coding sequence for the *Arabidopsis* bHLH-041 gene is set forth in SEQ ID NO: 5, and the amino acid sequence for the encoded bHLH-041 polypeptide is set forth in SEQ ID NO: 6.

In particular, the present invention provides for isolated polynucleotides comprising nucleotide sequences encoding the amino acid sequences shown in SEQ ID NOS: 3 and 6. Further provided are polypeptides having an amino acid sequence encoded by a polynucleotide described herein, for example those set forth in SEQ ID NOS: 1, 2 and 5, and fragments and variants thereof. The invention also provides isolated polynucleotides comprising the promoter sequence for the ELF3 gene from maize as set forth in SEQ ID NO: 4. Nucleic acid molecules comprising the complements of these nucleotide sequences are also provided. It is recognized that the coding sequence for the bHLH-041 gene (see, SEQ ID NO: 5) can be expressed in a plant for overexpression of the bHLH-041 transcription factor. However, for purposes of suppressing the shade-avoidance response of a plant, the coding sequence will be used to design constructs for suppression of expression of the bHLH-041 transcription factor. Thus, polynucleotides, in the context of suppressing the shade-avoidance response, refers to ELF3 coding sequences and to polynucleotides that when expressed suppress expression of the bHLH-041 gene, for example, via direct or indirect suppression as noted herein below.

Expression of the polynucleotides of the invention in plants prevents those plants from undergoing extensive reprogramming of their morphological development under limited light conditions, particularly when shaded by their neighbors or when grown in high density. Plants forage for light in plant canopies using a variety of photosensory systems. Far-red radiation reflected by neighbors is an early signal of competition that elicits anticipatory shade-avoidance responses. Shade-avoidance responses include symptoms such as promotion of stem and petiole elongation, reduced leaf thickness, reduced chlorophyll synthesis, accelerated flowering, and increased apical dominance. The shade-avoidance response reduces the availability of resources for storage and reproduction. Shade-avoidance is a mechanism where plants grown in close proximity respond to far-red (FR) radiation reflected from the leaves of neighboring plants by increasing significantly their stem length at the expense of leaf, fruit, and storage organ development, adversely affecting the yield of harvestable components. The shade-avoidance response may also have detrimental effects on ornamental plants grown indoors or in limited-light areas of a landscape.

FIG. 4 shows the effect of increasing population density on vegetative and reproductive development in *Arabidopsis*. Wild-type (Columbia) plants were grown under a range of densities (1: one plant in 4 cm$^2$; 2: one plant in 3 cm$^2$; 3 one plant in 2 cm$^2$; 4: one plant in 1 cm$^2$). With increased density, overall bolt height at flowering was reduced (panel A), number of bolts at flowering was reduced (B), leaf length was reduced (C), and silique length was reduced (D).

Plant density or population density varies from crop to crop as well as from growing region to growing region and year to year. The term "high density" or "high population density" is defined as a plant density at least about 10% higher than the average prevailing plant density of a given crop in a given growing region. In some embodiments, the high population density is at least 20% higher, at least 30% higher, at least 40% higher, at least 50% higher, at least 60% higher, at least 70% higher, at least 80% higher, at least 90% higher or at least 100% higher than the average prevailing density for the given crop in the given growing area. The "average prevailing density" is defined as the average plant density used by a majority of farmers in a region. For example, according to the National Agricultural Statistics Service of the United States Department of Agriculture, the average prevailing density for corn in ten Midwestern states in 2004 was 26,200 plants per acre (ppa). Thus for that region, high population density is preferably at least about 28,800, at least 30,000, at least 32,000, at least 34,000, at least 36,000, at least 38,000 or at least 40,000 plants per acre. It is recognized that planting density, i.e., number of seeds planted, will exceed the desired target plant population. For example, the average planting density for corn in North America in 2004 was 28,590 plants per acre.

The average prevailing densities of selected crop plants in the USA include corn at 20,000-29,000 plants per acre, wheat at 1,000,000-1,500,000 plants per acre, rice at 650,000-900,000 plants per acre, soy bean at 150,000-200,000 plants per acre, canola at 260,000-350,000 plants per acre, and sunflower at 17,000-23,00 plants per acre. In the same manner, average densities of any crop can be determined for any growing region.

By yield is intended the output or amount produced by a plant or crop. Yield can be measured in terms of number and/or size of fruit, seed, or other tissues harvested. Typically yield of crop plants is measured on a bushel-per-acre basis. Grain yield in agronomic crops is typically measured on a bushel-per-acre or kilogram-per-hectare basis.

An early flowering 3 (elf3) mutation was previously identified in *Arabidopsis*. It was proposed that ELF3 mediates an interaction between light and the circadian clock. Defects in ELF3 function lead to light-dependent arrhythmia. See, Covington, et al., (2001) *Plant Cell* 13:1305-1315, herein incorporated by reference. ELF3 appears to be an integral component of light input to the clock and likely gates both light input to the clock and acute induction of the circadian outputs by restricting the light sensitivity of these pathways in the evening. Overexpression of the ELF3 protein results in decreased sensitivity to the resetting stimulus, suggesting that ELF3 antagonizes light input to the clock during the night. ELF3 may represent a mechanism by which the oscillator modulates light resetting. Additionally, ELF3 proteins may be responsible for the circadian regulation of photoreceptor activity.

The invention provides maize ELF3 nucleotide sequences (SEQ ID NOS: 1 and 2) and an ELF3 protein encoded thereby (SEQ ID NO: 3). The maize ELF3 protein (also referred to as ZM-ELF3) shares 19.4% identity with the *Arabadopsis thaliana* ELF3 protein designated At2g25930 (SEQ ID NO: 7; GenBank Accession No. NM_128153; see also, SEQ ID NO: 2 of U.S. Pat. No. 6,903,192), with four conserved regions across these two sequences (see, the alignment in FIG. 1; region I, corresponding to residues 20-57 of SEQ ID NO: 3; region II, corresponding to residues 362 to 410 of SEQ ID NO: 3; region III, corresponding to residues 516-535 of SEQ ID NO: 3; and region IV, corresponding to residues 728-754 of SEQ ID NO: 3) that are shared among previously identified ELF3 proteins (see, Liu, et al., (2001) *Plant Cell* 13:1293-1304, herein incorporated by reference). PFAM analysis reveals a domain within region II with similarity to Ribosome-binding factor A (InterPRO PS01319 IPR000238) suggesting that ELF3 may perform functions related to control of protein synthesis.

The ZM-ELF3 protein also shares homology with other proteins, for example, the putative early flowering 3 protein from *Oryza sativa*, included in the alignment shown in FIG. 1 (SEQ ID NO: 8; see also, GenBank Accession No. BAA83571; coding sequence shown in GenBank Accession No. AP000399); putative early flowering 3 protein from *Oryza sativa* (derived from BAA83571; see, GenBank Accession No. XP_493738; coding sequence shown in GenBank Accession No. XM_493738); hypothetical protein designated P0697C12.15 from *Oryza sativa* (GenBank Accession No. NP_918455; coding sequence shown in GenBank Accession No. NM_193566.1); nematode responsive protein-like protein from *Oryza sativa* (GenBank No. BAD45081; coding sequence shown in GenBank Accession No. AP003296); early flowering 3 protein from *Mesembryanthemum crystallinum* (GenBank Accession No. AAQ73529; coding sequence shown in GenBank Accession No. AY371292; the sequence for an unknown protein from *Arabidopsis thaliana* (GenBank Accession No. AAM15042; coding sequence shown in GenBank Accession No. AC005395); hypothetical protein At3g21320 from *Arabidopsis thaliana* (GenBank Accession No. AAX23847; coding sequence shown in GenBank Accession No. AY924772; hypothetical protein AT3G21320 from *Arabidopsis thaliana* (GenBank Accession No. AAV68859; coding sequence shown in GenBank Accession No. AY800623); nematode responsive protein from *Arabidopsis thaliana* (GenBank Accession No. CAA72719; coding sequence shown in GenBank Accession No. Y11994; ELF3 homologue from *Lemna gibba* (GenBank Accession No. BAD97872; coding sequence shown in GenBank Accession No. AB210851; and an unnamed protein product from *Arabidopsis thaliana* (GenBank Accession No. BAB01726; coding sequence shown in GenBank Accession No. AB023045).

The methods of the invention include expression of the ELF3 sequence of the invention in a plant of interest. While not bound by any mechanism of action, expression/overexpression of the ELF3 sequence inhibits or suppresses the plant shade-avoidance response. In this manner, a plant can be transformed with a DNA construct comprising a promoter operably linked to a nucleotide sequence comprising the ELF3 coding sequence (e.g., nucleotides 167-2443 of SEQ ID NO: 1, set forth as SEQ ID NO: 2) or fragment or variant thereof, increasing the level or activity of the ELF3 polypeptide. A promoter may be chosen to express the sequence in select tissues, at select times, or for constitutive expression.

In response to shade, horizontal blue light gradients guide plant shoots to canopy gaps in patchy vegetation. These B light signals are perceived by specific photoreceptors. Plants possess at least two types of photoreceptors whose main physiological function is the acquisition of information. One of these, the phytochromes, absorb maximally in the red (R) and far-red (FR) regions of the spectrum. Phytochromes are regulatory proteins that control plant gene expression in response to light. Recent work has demonstrated the conservation of photoreceptor function across divergent evolutionary boundaries.

The phytochromes are a family of plant photoreceptor proteins that control several adaptive developmental strategies. For example, the phytochromes perceive far-red light (wave lengths between 700 and 800 nm) reflected or scattered from the leaves of nearby vegetation. This provides an early warning of potential shading, and triggers a series of shade-avoidance responses by which the plant attempts to outgrow its neighbors. The circadian clock gates this rapid shade-avoidance response. (See, e.g., Blazquez, et al., (2000) *J. Cell. Sci.* 113:3547). One of the rapidly responsive genes encodes a basic helix-loop-helix protein. The gene product is required for the accelerated growth associated with the shade-avoidance response.

The basic helix-loop-helix (bHLH) proteins are a superfamily of transcription factors that bind as dimers to specific DNA target sites. The family is defined by the bHLH signature domain, which consists of about 60 amino acids with two functionally distinct regions. The basic region is located at the N-terminal end of the domain and is involved in DNA binding. The basic region consists of about 15 amino acids including a high number of basic residues. The HLH region is located at the C-terminal end and functions as a dimerization domain. The HLH region consists mainly of hydrophobic residues that form two amphipathic α-helices separated by a loop region of variable sequence and length. Outside of the conserved bHLH signature domain, the proteins exhibit considerable sequence divergence.

The bHLH genes have been studied in *Arabidopsis* and over 140 genes have been identified, constituting one of the largest families of transcription factors in *Arabidopsis*. See, Toledo-Ortiz, et al., (2003) *Plant Cell* 15:1749-1770, herein incorporated by reference. Twenty-one sub-families have been identified having conserved amino acid sequence motifs outside the DNA binding domain. It is predicted that this family of transcription factors has a diverse range of roles in plant cell and tissue development as well as plant metabolism. Some bHLH proteins (e.g., PIF3 and related bHLH proteins; see, for example, Ni, et al., (1998) *Cell* 95(5):657-667) physically interact with phytochrome. In addition, a related bHLH, called PIL1, is involved in the circadian clock (see, for example, Makino, et al., (2002) *Plant Cell Physiol.* 43(1):58-69 and Salter, et al., (2003) *Nature* 426(6967):680-683).

The invention provides the *Arabidopsis thaliana* bHLH-041 nucleotide sequence (SEQ ID NO: 5) and the bHLH-041 protein encoded thereby (SEQ ID NO: 6). The bHLH-041 protein shares homology with a number of bHLH proteins, including, for example, a bHLH-like protein from *Oryza sativa* (GenBank Accession No. BAD61929; coding sequence shown in GenBank Accession No. AP005460); the protein designated as B1112D09.4 from *Oryza sativa* (GenBank Accession No. NP_918505; coding sequence shown in GenBank Accession No. NM_193616); another bHLH-like protein from *Oryza sativa* (GenBank Accession No. BAD72434; coding sequence shown in report for GenBank Accession No. AP003417); the protein designated as P0498B01.27 from *Oryza sativa* (GenBank Accession No. NP_913134; coding sequence shown in GenBank Accession No. NM_188245); another bHLH-like protein from *Oryza sativa* (GenBank Accession No. BAD72431; coding sequence shown in report for GenBank Accession No. AP003417); the protein designated as P0498B01.20 from *Oryza sativa* (GenBank Accession No. NP_913129; coding sequence shown in GenBank Accession No. NM_188240); another bHLH-like protein from *Oryza sativa* (GenBank Accession No. BAD72430; coding sequence shown in report for GenBank Accession No. AP003417); the protein designated as P0498B01.17 from *Oryza sativa* (GenBank Accession No. NP_913126; coding sequence shown as GenBank Accession No. NM_188237); the bHLH protein family-like protein from *Oryza sativa* (GenBank Accession No. XP_464694; coding sequence shown in GenBank Accession No. XM_464694); and the sequence for an unknown protein from *Arabidopsis thaliana* (GenBank Accession No. AAM63723; coding sequence shown in GenBank Accession No. AY086666).

While not being bound by theory or mechanism of action, it is believed that the bHLH transcription factor of the invention, bHLH-041 (shown in SEQ ID NO: 6), interacts with phytochromes involved in light perception. Therefore, suppression of expression of the bHLH-041 gene or genes for other members of the transcription factor class would prevent interaction with phytochromes and suppress the plant shade-avoidance response. In this manner, the invention provides for suppressing the expression of the bHLH-041 gene or genes for similar transcription factors that act in the same manner. Therefore, for purposes of suppression of the shade-avoidance response, bHLH-041 polynucleotides include those polynucleotides that when expressed in a plant suppress the expression of the bHLH-041 gene or genes for similar transcription factors that act on phytochromes. Expression of the polynucleotide reduces or eliminates the level or activity of bHLH-041 in a plant. The expression may reduce or eliminate the level of bHLH-041 in any of various ways; for example, by influencing the level of bHLH-041 RNA transcript; by influencing translation and thereby affecting the level of the encoded bHLH-041 polypeptide; or by interfering with the function of the encoded bHLH-041 polypeptide, such as by competitive binding to a DNA target sequence.

It is recognized that RNA suppression sequences, as discussed below, may be designed to specifically target bHLH-041 gene expression or alternatively target genes for those transcription factors sharing homology with bHLH-041. In this manner, for selective suppression of the bHLH-041 protein, suppression sequences will be designed based on sequences outside of the conserved bHLH signature domain of this protein, which resides at residues 287-339 of SEQ ID NO: 6. bHLH is a helix-loop-helix transcription factor and as such has a basic region (PFAM: PF00010; IPR001092) that determines specificity of interaction with regulatory regions of target genes. In the case of bHLH-041, the basic region (SERKRREKLN; residues 293-302 of SEQ ID NO: 6) is the most conserved and is diagnostic of this group of transcription factors.

The ELF3 and bHLH-041 polynucleotides of the invention may be used alone or in combination to decrease or reduce the plant shade-avoidance response in plants and increase yield in plants. That is, the methods of the invention prevent the shade-avoidance response of plants and counterbalance the effects of asymmetric competition for light. The methods have important implications for the yield-density and productivity-density relationships of plants. The plants of the invention exhibit altered photomorphogenesis and improved yield but do not exhibit the characteristics of typical plants grown in high-density settings.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of the native protein and hence have ELF3 protein or bHLH-041 protein activity. Measurement of bHLH-041 protein activity is described elsewhere herein. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotide encoding the proteins of the invention.

A fragment of an ELF3 polynucleotide that encodes a biologically active portion of an ELF3 protein of the invention will encode at least 15, 25, 30, 50, 100, 150, 200, 250, 300, 350, 400, 450, 500, 550, 600, 650, 700, 750 contiguous amino acids or up to the total number of amino acids present in a full-length ELF3 protein of the invention (for example, 759 amino acids for SEQ ID NO: 3). In some embodiments, a fragment of an ELF3 polynucleotide that encodes a biologically active portion of an ELF3 protein of the invention will encode an ELF3 polypeptide fragment comprising at least region I, corresponding to residues 20-57 of SEQ ID NO: 3, at least region II, corresponding to residues 362 to 410 of SEQ ID NO: 3, at least region III, corresponding to residues 516-535 of SEQ ID NO: 3, at least region IV, corresponding to residues 728-754 of SEQ ID NO: 3), or any combination of regions I, II, III, and IV of SEQ ID NO: 3, where each of these regions is encoded by the corresponding codons set forth in SEQ ID NO: 2 or alternative codons due to the degeneracy of the genetic code. Thus, for example, the encoded ELF3 polypeptide fragment could comprise residues corresponding to regions I and II of SEQ ID NO: 3, regions I and III of SEQ ID NO:3, regions I and IV of SEQ ID NO:3, regions I, II, and III of SEQ ID NO: 3, regions I, III, and IV of SEQ ID NO: 3, regions I, II, III, and IV of SEQ ID NO: 3, regions II and III of SEQ ID NO: 3, regions II and IV of SEQ ID NO: 3, regions II, III, and IV of SEQ ID NO: 3, or regions III and IV of SEQ ID NO: 3, where each of these regions is encoded by the corresponding codons set forth in SEQ ID NO: 2 or alternative codons due to the degeneracy of the genetic code. However, fragments of a polynucleotide of the invention that are useful as hybridization probes or PCR primers generally need not encode a biologically active portion of an ELF3 protein.

A fragment of a bHLH-041 polynucleotide that encodes a biologically active portion of a bHLH-041 protein of the invention will encode at least 15, 25, 30, 50, 100, 150, 200, 250, 300, 350, 400, 450 contiguous amino acids, or up to the total number of amino acids present in a full-length bHLH-041 protein of the invention (for example, 466 amino acids for SEQ ID NO: 6). In some embodiments, a fragment of a bHLH-041 polynucleotide that encodes a biologically active portion of a bHLH-041 protein of the invention will encode a bHLH-041 polypeptide fragment comprising at least the basic region of the bHLH signature domain, where the basic region corresponds to residues 293-302 of SEQ ID NO: 6, at least the HLH region of the bHLH signature domain, where the bHLH signature domain corresponds to residues 287-339 of SEQ ID NO: 6, or both of these regions, where each of these regions is encoded by the corresponding codons set forth in SEQ ID NO: 5 or alternative codons due to the degeneracy of the genetic code. In other embodiments, a fragment of a bHLH-041 polynucleotide that encodes a biologically active portion of a bHLH-041 protein of the invention will encode a polypeptide comprising the bHLH signature domain, corresponding to residues 287-339 of SEQ ID NO: 6, where this region is encoded by the corresponding codons set forth in SEQ ID NO: 5 or alternative codons due to the degeneracy of the genetic code. However, fragments of a polynucleotide of the invention that are useful as hybridization probes or PCR primers generally need not encode a biologically active portion of a bHLH-041 protein.

Thus, a fragment of an ELF3 or bHLH-041 polynucleotide may encode a biologically active portion of an ELF3 or bHLH-041 protein, respectively, or it may be a fragment that can be used as a hybridization probe or PCR primer using methods disclosed below. A biologically active portion of an ELF3 or bHLH-041 protein can be prepared by isolating a portion of one of the ELF3 or bHLH-041 polynucleotides of the invention, respectively, expressing the encoded portion of the ELF3 or bHLH-041 protein (e.g., by recombinant expression in vitro), and assessing the activity of the encoded portion of the ELF3 or bHLH-041 polypeptide. Polynucleotides that are fragments of an ELF3 or bHLH-041 nucleotide sequence comprise at least 16, 20, 50, 75, 100, 150, 200, 250, 300, 350, 400, 450, 500, 550, 600, 650, 700, 800, 900, 1,000, 1,100, 1,200, 1,300 or 1,400 contiguous nucleotides, or up to the number of nucleotides present in a full-length ELF3 or bHLH-041 polynucleotide disclosed herein (for example, 2496, 2277, and 1401 nucleotides for SEQ ID NOS: 1, 2 and 5, respectively).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the ELF3 or bHLH-041 polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an ELF3 or bHLH-041 protein of the invention. Generally, variants of a particular polynucleotide of the invention (for example, SEQ ID NO: 1, SEQ ID NO: 2, or SEQ ID NO: 5) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the ELF3 or bHLH-041 polypeptide of SEQ ID NO: 3 or SEQ ID NO: 6, respectively, is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein, that is, transcription factor activity for bHLH-041 and regulation of photoreceptor activity for ELF3 as described herein. Such variants may result from, for example, genetic polymorphism or from human manipulation. Biologically active variants of a native ELF3 or bHLH-041 protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The proteins of the invention may be altered in various ways including amino acid substitutions, deletions, truncations, and insertions. Methods for such manipulations are generally known in the art. For example, amino acid sequence variants and fragments of the ELF3 and bHLH-041 proteins can be prepared by mutations in the DNA. Methods for mutagenesis and polynucleotide alterations are well known in the art. See, for example, Kunkel (1985) *Proc. Natl. Acad. Sci.*

USA 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by routine transgenic plant analysis, observed as a disruption in the plant density response or appearance of a desired phenotypic change, such as inhibition of the shade-avoidance response and increased tolerance to plant density.

Variant polynucleotides and proteins also encompass sequences and proteins derived from a mutagenic and recombinogenic procedure such as DNA shuffling. With such a procedure, one or more different ELF3 or bHLH-041 coding sequences can be manipulated to create a new ELF3 or bHLH-041 protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the ELF3 or bHLH-041 gene of the invention and other known ELF3 or bHLH transcription factor genes, respectively, to obtain a new gene coding for a protein with an improved property of interest. Strategies for such DNA shuffling are known in the art. See, for example, Stemmer (1994) *Proc. Natl. Acad. Sci. USA* 91:10747-10751; Stemmer (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

The compositions of the invention also include isolated nucleic acid molecules comprising the maize ELF3 promoter (also referred to as the ZM-ELF3 promoter) nucleotide sequence set forth in SEQ ID NO: 4. By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. Such elements include a putative CAAT element present at nucleotides 402-405 of SEQ ID NO: 4. In addition six sequence motifs with approximately 50% identity to the "evening element motif," which is correlated with circadian control of plant genes, are present within the upstream ZM-ELF3 sequence. See, FIG. 3.

It is recognized that having identified the nucleotide sequence for the promoter region disclosed herein, it is within the state of the art to isolate and identify additional regulatory elements in the 5' untranslated region upstream from the particular promoter region defined herein. Thus for example, the promoter region disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618.

Fragments and variants of the disclosed ZM-ELF3 promoter nucleotide sequence are also encompassed by the present invention. By "fragment" is intended a portion of the nucleotide sequence. Fragments of a promoter nucleotide sequence may retain biological activity and hence retain their transcriptional regulatory activity. Thus, for example, less than the entire promoter sequence disclosed herein may be utilized to drive expression of an operably linked nucleotide sequence of interest, such as a nucleotide sequence encoding a heterologous protein. Alternatively, fragments of a promoter nucleotide sequence that are useful as hybridization probes generally do not retain biological activity. Thus, fragments of a promoter nucleotide sequence may range from at least about 20 nucleotides, about 50 nucleotides, about 100 nucleotides, and up to the full-length promoter nucleotide sequence of the invention.

Thus, a fragment of an ELF3 promoter nucleotide sequence may encode a biologically active portion of the ELF3 promoter, or it may be a fragment that can be used as a hybridization probe or PCR primer using methods disclosed below. A biologically active portion of an ELF3 promoter can be prepared by isolating a portion of one of the ELF3 promoter nucleotide sequences of the invention, and assessing the activity of the portion of the ELF3 promoter. Nucleic acid molecules that are fragments of an ELF3 promoter nucleotide sequence comprise at least 16, 20, 50, 75, 100, 150, 200, 250, 300, 350, 400, 450 nucleotides or up to the number of nucleotides present in a full-length ELF3 promoter nucleotide sequence disclosed herein (for example, 459 nucleotides for the ZM-ELF3 promoter shown in SEQ ID NO: 4). Assays to determine the activity of a promoter sequence are well known in the art. For example, an ELF3 promoter fragment or variant may be operably linked to the nucleotide sequence encoding any reporter protein, such as the β-glucuronidase protein (GUS reporter) or the luciferase protein. The DNA construct is inserted into the genome of a plant or plant cell, and the mRNA or protein level of the reporter sequence is determined. See, for example, Eulgem, et al., (1999) *EMBO Journal* 18:4689-4699.

The polynucleotides of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire ELF3 or bHLH-041 sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode an ELF3 or bHLH-041 protein, or isolated polynucleotides that confer promoter activity, and which hybridize under stringent conditions to the respective ELF3 or bHLH-041 nucleotide sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the ELF3 or bHLH-041 polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, an entire ELF3 or bHLH-041 polynucleotide disclosed herein, or one or more portions thereof, may be used as a probe capable of specifically hybridizing to corresponding elf3 or bHLH-041 polynucleotides and messenger RNAs. To achieve specific hybridization under a variety of conditions, such probes include sequences that are unique among ELF3 or bHLH-041 polynucleotide sequences and are optimally at least about 10 nucleotides in length, and most optimally at least about 20 nucleotides in length. Such probes may be used to amplify corresponding polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith, et al., (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul (1990), supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package (Accelrys, Inc., San Diego, Calif.) for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The ELF3 and bHLH-041 polynucleotides can be provided in expression cassettes for expression in the plant of interest. As indicated above, for suppression of the shade-avoidance response, for manipulation of levels of ELF3, the cassettes will provide for expression of the ELF3 polypeptide while for manipulation of levels of bHLH-041, the constructs will be prepared to suppress the expression of the bHLH-041 polypeptide in transgenic plants. The cassette will include 5' and 3' regulatory sequences operably linked to an ELF3 coding sequence or a polynucleotide that when expressed is capable of reducing or eliminating expression of the bHLH polypeptide of the invention or related bHLH transcription factor. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will generally include in the 5'-3' direction of transcription, a transcriptional and translational initiation region (i.e., a promoter), a polynucleotide of the invention, and a transcriptional and translational termination region (i.e., termination region) functional in plants. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

While it may be optimal to express the sequences using heterologous promoters, the native promoter sequences may be used. Such constructs can change expression levels of ELF3 or bHLH-041 in the plant or plant cell. Thus, the phenotype of the plant or plant cell can be altered.

The termination region may be native with the transcriptional initiation region, may be native with the operably linked polynucleotide of interest, may be native with the plant host, or may be derived from another source (i.e., foreign or heterologous to the promoter, the polynucleotide of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, N.Y.), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention, including the native promoter of the polynucleotide sequence of interest. The promoters can be selected based on the desired outcome. That is, the nucleic acids can be combined with constitutive promoters, tissue-preferred promoters, including but not limited to leaf-preferred promoters, light-regulated or light-inducible promoters, circadian clock-regulated promoters, or other promoters for expression in plants. Constitutive or vegetative-tissue-preferred promoters would be preferred.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; 6,177,611; 6,670,467; and 6,504,083.

Tissue-preferred promoters can be utilized to target expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590; and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; and Matsuoka, et al., (1993) *Proc. Natl. Acad. Sci. USA* 90(20):9586-9590.

Light-regulated or light-inducible promoters provide for expression of operably linked nucleotide sequences in response to quantity and/or quality of light in the plant's environment. Light-regulated promoters are known in the art, including, but not limited to, the ribulose bisphosphate carboxylase (Rubisco) small subunit (rbcS) gene promoters from a variety of species (see, for example, Kyozuka, et al., (1993) *Plant Physiol.* 102:991-1000 discussing the rice and tomato rbcS promoters; Bansal, et al., (1992) *Proc. Natl. Acad. Sci.* 89:3654-3658, and Schaffner and Sheen (1991) *Plant Cell* 3(9):997-1012, both discussing the maize rbcS promoter; and Timko, et al., (1985) *Nature* 318:579-582, and Coruzzi, et al., (1984) *EMBO J.* 3(8):1671-1679, both discussing the pea rbcS promoter); phosphoenolpyruvate carboxylase (PEPC) gene promoters (see, for example, Matsuoka, et al., (1994) *Plant J.* 6(3):311-319 discussing the PEPC promoter from maize); chlorophyll a/b binding protein gene promoters (see, for example, Bansal, et al., (1992) *Proc. Natl. Acad. Sci.* 89:3654-3658 discussing the maize cab-m1 promoter sequence); and the like.

Other promoters of interest include, but are not limited to, promoters that are responsive to circadian rhythms, referred to herein as circadian clock-regulated promoters. Examples include, but are not limited to, promoters of genes of the light-harvesting complex (LHC) (see, for example, Piechulla (1998) *Chronobiol. Int.* 16(2):15-128 and Piechulla, et al., (1998) *Plant Mol. Biol.* 38(4):655-662); chalcone synthase (CHS) promoters (see, for example, Thain, et al., (2002) *Plant Physiol.* 130(1):102-110); phytochrome and cryptochrome gene promoters (see, for example, Tóth, et al., (2001) *Plant Physiol.* 127:1607-1616; and the like.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-28), cyanofluorescent protein (CYP) (Bolte, et al., (2004) *J. Cell Science* 117:943-54 and Kato, et al., (2002) *Plant Physiol.* 129:913-42), and yellow fluorescent protein (PhiYFP™ from Evrogen, see, Bolte, et al., (2004) *J. Cell Science* 117:943-54). For additional selectable markers, see generally, Yarranton (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff (1992) *Mol. Microbiol.* 6:2419-2422; Barkley, et al., (1980) *The Operon*, pp. 177-220; Hu, et al., (1987) *Cell* 48:555-566;

Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference.

The above list of selectable marker genes is not meant to be limiting. Any selectable marker gene can be used in the present invention.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski, et al., (1984) *EMBO J.* 3:2717-2722), and ballistic particle acceleration (see, for example, U.S. Pat. Nos. 4,945,050; U.S. Pat. No. 5,879,918; U.S. Pat. Nos. 5,886,244; and, 5,932,782; Tomes, et al., (1995) in *Plant Cell, Tissue, and Organ Culture: Fundamental Methods*, ed. Gamborg and Phillips (Springer-Verlag, Berlin); McCabe, et al., (1988) *Biotechnology* 6:923-926); and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783; and, 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that an ELF3 or bHLH-041 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta, et al., (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant cell includes plant protoplasts, as well as cells in plant tissue cultures from which plants can be regenerated, including plant calli and plant clumps. Plant cells may be intact in plants or parts of plants such as embryos, pollen, ovules, seeds, leaves, flowers, branches, fruit, kernels, ears, cobs, husks, stalks, roots, root tips, anthers, and the like.

Grain is intended to mean the mature seed produced by commercial growers for purposes other than growing or reproducing the species.

Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, Brassica, soybean, cotton, safflower, peanut, sorghum, wheat, millet, tobacco, etc.). In other embodiments, corn and soybean plants are optimal, and in yet other embodiments corn plants are optimal.

A "subject plant" or "subject plant cell" is one in which genetic alteration, such as transformation, has been effected as to a gene of interest, or is a plant or plant cell which is descended from a plant or plant cell so altered and which comprises the alteration. A "control" or "control plant" or "control plant cell" provides a reference point for measuring changes in the subject plant or plant cell.

A control plant or control plant cell may comprise, for example: (a) a wild-type plant or plant cell, i.e., of the same genotype as the starting material for the genetic alteration which resulted in the subject plant or subject plant cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or subject plant cell; (d) a plant or plant cell genetically identical to the subject plant or subject plant cell but which is not exposed to conditions or stimuli that would induce expression of the gene of interest; or (e) the subject plant or subject plant cell itself, under conditions in which the gene of interest is not expressed.

In certain species, such as maize, the control and reference plants may represent two hybrids, where the first hybrid is produced from two parent inbred lines, and the second hybrid is produced from the same two parental inbred lines except that one of the parent inbred lines contains a recombinant DNA construct. Performance of the second hybrid would typically be measured relative to the first hybrid.

Further, where a plant comprising a recombinant DNA construct is assessed or measured relative to a control plant not comprising the recombinant DNA but otherwise having a comparable genetic background to the plant, the control and reference plant may share at least 90%, 91%, 92%, 93%, 94%, 95%, 96%, 97%, 98%, 99% or 100% sequence identity of nuclear genetic material. There are many laboratory-based techniques available for the analysis, comparison and characterization of plant genetic backgrounds; among these are isozyme electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as microsatellites.

In the present case, for example, in various embodiments, changes in ZmELF3 or bHLH-041 activity, and/or changes in one or more traits such as leaf size or shape, seed production, stem or petiole elongation, chlorophyll synthesis, or branching could be measured by comparing a subject plant or subject plant cell to a control plant or control plant cell.

A method is provided for modulating the concentration and/or activity of the ELF3 polypeptide of the present invention, i.e. ZmELF3 protein activity, in a plant. In general, concentration and/or activity is increased by at least 1%, 5%, 10%, 20%, 30%, 40%, 50%, 60%, 70%, 80% or 90% relative to a native control plant, plant part, or plant cell that did not have the sequence of the invention introduced. Modulation in the present invention may occur in a temporal or developmental pattern. In specific embodiments, the polypeptides of the present invention are increased in crop plants.

The expression level of the ELF3 polypeptide may be measured directly, for example, by assaying for the level of the ELF3 polypeptide in the plant or plant cell, or indirectly, for example, by determining the effect in a transgenic plant at the phenotypic level, i.e., by transgenic plant analysis, observed as a disruption in the plant density response or the appearance of a desired phenotypic change, such as inhibition of the shade-avoidance response and increased tolerance to plant density.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

In some embodiments, the activity of the bHLH-041 polypeptide of the invention, or its ortholog, is reduced or eliminated by transforming a plant cell with an expression cassette that expresses a polynucleotide that inhibits the expression of bHLH-041. The polynucleotide may inhibit the expression of bHLH-041 directly, by preventing transcription or translation of the bHLH-041 messenger RNA, or indirectly, by encoding a polypeptide that inhibits the transcription or translation of a gene encoding bHLH-041, or by encoding a polypeptide that interferes with function of the endogenous bHLH-041 protein. Methods for inhibiting or eliminating the expression of a gene in a plant are well known in the art, and any such method may be used in the present invention to inhibit the expression of bHLH-041, thereby altering bHLH-041 protein activity.

In accordance with the present invention, the expression of a bHLH-041 gene is inhibited if the protein level of the bHLH-041 is statistically lower than the protein level of the same bHLH-041 in a plant that has not been genetically modified or mutagenized to inhibit the expression of that bHLH-041. In particular embodiments of the invention, the protein level of the bHLH-041 in a modified plant according to the invention is less than 95%, less than 90%, less than 80%, less than 70%, less than 60%, less than 50%, less than 40%, less than 30%, less than 20%, less than 10%, or less than 5% of the protein level of the same bHLH-041 in a plant that is not a mutant or that has not been genetically modified to inhibit the expression of that bHLH-041. The expression level of the bHLH-041 may be measured directly, for example, by assaying for the level of bHLH-041 expressed in the plant cell or plant, or indirectly, for example, by observing the effect in a transgenic plant at the phenotypic level, i.e., by transgenic plant analysis, observed as a disruption in the plant density response or the appearance of a desired phenotypic change, such as inhibition of the shade-avoidance response and increased tolerance to plant density.

In addition, or in the alternative, the expression level of bHLH-041 may be measured indirectly by monitoring expression level of genes whose expression is modulated by the expression of bHLH-041. In this manner, changes in the expression level of these related genes would be indicative of changes in expression level of bHLH-041, and thus these related genes could serve as markers for bHLH-041 activity. Without being bound by theory, examples of such related genes could include ELF3 itself or light and circadian rhythm genes (for example, phytochromes, catalase, nitrate reductase).

In other embodiments of the invention, the activity of bHLH-041 is reduced or eliminated by transforming a plant cell with an expression cassette comprising a polynucleotide encoding a polypeptide that inhibits the activity of bHLH-041. The activity of a bHLH-041 is inhibited according to the present invention if the activity of the bHLH-041 is statistically lower than the activity of the same bHLH-041 in a plant that has not been genetically modified to inhibit the activity of that bHLH-041. In particular embodiments of the invention, the activity of the bHLH-041 in a modified plant according to the invention is less than 95%, less than 90%, less than 80%, less than 70%, less than 60%, less than 50%, less than 40%, less than 30%, less than 20%, less than 10% or less than 5% of the activity of the same bHLH-041 in a plant that has not been genetically modified to inhibit the expression of that bHLH-041. The activity of a bHLH-041 is "eliminated" according to the invention when it is not detectable by the assay methods described elsewhere herein.

In other embodiments, the activity of a bHLH-041 may be reduced or eliminated by disrupting the gene encoding the bHLH-041 protein. The invention encompasses mutagenized plants that carry mutations in bHLH-041 genes, where the mutations reduce expression of the bHLH-041 gene or inhibit the activity of the encoded bHLH-041.

Thus, many methods may be used to reduce or eliminate the activity of a bHLH-041. More than one method may be used to reduce the activity of a single plant bHLH-041. Non-limiting examples of methods of reducing or eliminating the expression of a plant bHLH-041 are given below.

In some embodiments of the present invention, a plant cell is transformed with an expression cassette that is capable of expressing a polynucleotide that inhibits the expression of bHLH-041. The term "expression" as used herein refers to the biosynthesis of a gene product, including the transcription and/or translation of said gene product. For example, for the purposes of the present invention, an expression cassette capable of expressing a polynucleotide that inhibits the expression of at least one bHLH-041 is an expression cassette capable of producing an RNA molecule that inhibits the transcription and/or translation of at least one bHLH-041. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a bHLH-041 are given below.

In some embodiments of the invention, inhibition of the expression of bHLH-041 may be obtained by sense suppression or cosuppression. For cosuppression, an expression cassette is designed to express an RNA molecule corresponding to all or part of a messenger RNA encoding a bHLH-041 in the "sense" orientation. Overexpression of the RNA molecule can result in reduced expression of the native gene. Accordingly, multiple plant lines transformed with the cosuppression expression cassette are screened to identify those that show the greatest inhibition of bHLH-041 expression.

The polynucleotide used for cosuppression may correspond to all or part of the sequence encoding the bHLH-041, all or part of the 5' and/or 3' untranslated region of a bHLH-041 transcript, or all or part of both the coding sequence and the untranslated regions of a transcript encoding bHLH-041. In some embodiments where the polynucleotide comprises all or part of the coding region for the bHLH-041 protein, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dt region in the expression cassette at a position 3' to the sense sequence and 5' of the polyadenylation signal. See, U.S. Patent Publication No. 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

In some embodiments of the invention, inhibition of the expression of bHLH-041 may be obtained by antisense suppression. For antisense suppression, the expression cassette is designed to express an RNA molecule complementary to all or part of a messenger RNA encoding the bHLH-041 polypeptide. Overexpression of the antisense RNA molecule can result in reduced expression of the native gene. Accordingly, multiple plant lines transformed with the antisense suppression expression cassette are screened to identify those that show the greatest inhibition of bHLH-041 expression.

The polynucleotide for use in antisense suppression may correspond to all or part of the complement of the sequence encoding the bHLH-041, all or part of the complement of the 5' and/or 3' untranslated region of the bHLH-041 transcript, or all or part of the complement of both the coding sequence and the untranslated regions of a transcript encoding the bHLH-041. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dt region in the expression cassette at a position 3' to the antisense sequence and 5' of the polyadenylation signal. See, U.S. Patent Publication No. 2002/0048814, herein incorporated by reference.

In some embodiments of the invention, inhibition of the expression of a bHLH-041 may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of bHLH-041 expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

In some embodiments of the invention, inhibition of the expression of bHLH-041 may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk, et al., (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk, et al., (2002) *Plant Physiol.* 129:1723-1731; Waterhouse and Helliwell (2003) *Nat. Rev. Genet.* 4:29-38; Pandolfini, et al., *BMC Biotechnology* 3:7, and U.S. Patent Publication No. 20030175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz, et al., (2002) *PNAS* 99 (Suppl. 4):16499-16506; Mette, et al., (2000) *EMBO J* 19(19):5194-5201).

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for bHLH-041). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

In some embodiments, the polynucleotide expressed by the expression cassette of the invention is catalytic RNA or has ribozyme activity specific for the messenger RNA of bHLH-041. Thus, the polynucleotide causes the degradation of the endogenous messenger RNA, resulting in reduced expression of the bHLH-041. This method is described, for example, in U.S. Pat. No. 4,987,071, herein incorporated by reference.

In some embodiments of the invention, inhibition of the expression of bHLH-041 may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier et al., (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of bHLH-041 expression, the 22-nucleotide sequence is selected from a bHLH-041 transcript sequence and contains 22 nucleotides of said bHLH-041 sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In one embodiment, the polynucleotide encodes a zinc finger protein that binds to a gene encoding a bHLH-041, resulting in reduced expression of the gene. In particular embodiments, the zinc finger protein binds to a regulatory region of a bHLH-041 gene. In other embodiments, the zinc finger protein binds to a messenger RNA encoding a bHLH-041 and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355; each of which is herein incorporated by reference.

In some embodiments of the invention, the polynucleotide encodes an antibody that binds to at least one bHLH-041, and reduces the activity of the bHLH-041. In another embodiment, the binding of the antibody results in increased turnover of the antibody-bHLH-041 complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

In other embodiments, a dominant negative approach to downregulation is employed, wherein a plant is transformed with a polynucleotide encoding a partial bHLH-041 transcription factor. The encoded partial transcription factor, which may be lacking the DNA binding domain or the trans-activating domain, competes for binding sites, reducing the functional effect of the native transcription factor. See, for example, Kuhlmann, et al., (2003) *J. Biol. Chem.* 278(10): 8786-8794; Heinekamp, et al., (2004) *Plant J.* 38:298-309; King, et al., (1999) *Internat'l. Immun.* 11(8):1203-1215.

In some embodiments of the present invention, the activity of bHLH-041 is reduced or eliminated by disrupting the gene encoding the bHLH-041. The gene encoding the bHLH-041 may be disrupted by any method known in the art. For example, in one embodiment, the gene is disrupted by transposon tagging. In another embodiment, the gene is disrupted by mutagenizing plants using random or targeted mutagenesis, and selecting for plants that have reduced bHLH-041 activity.

In one embodiment of the invention, transposon tagging is used to reduce or eliminate the activity of bHLH-041. Transposon tagging comprises inserting a transposon within an endogenous bHLH-041 gene to reduce or eliminate expression of the bHLH-041. "bHLH-041 gene" is intended to mean the gene that encodes a bHLH-041 according to the invention.

In this embodiment, the expression of bHLH-041 is reduced or eliminated by inserting a transposon within a regulatory region or coding region of the gene encoding the bHLH-041. A transposon that is within an exon, intron, 5' or 3' untranslated sequence, a promoter, or any other regulatory sequence of a bHLH-041 gene may be used to reduce or eliminate the expression and/or activity of the encoded bHLH-041.

Methods for the transposon tagging of specific genes in plants are well known in the art. See, for example, Maes, et al., (1999) *Trends Plant Sci.* 4:90-96; Dharmapuri and Sonti (1999) *FEMS Microbiol. Lett.* 179:53-59; Meissner, et al., (2000) *Plant J.* 22:265-274; Phogat, et al., (2000) *J. Biosci.* 25:57-63; Walbot (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima, et al., (1998) *Virology* 243: 472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of bHLH-041. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other Bacillus thuringiensis toxic proteins (described in U.S. Pat. Nos. 5,366,892; 5,747,450; 5,737,514; 5,723,756; 5,593,881; and Geiser, et al., (1986) *Gene* 48:109), lectins (Van Damme, et al., (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson, et al., (1987) *Eur. J. Biochem.* 165:99-106; and WO 98/20122) and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see, U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The nucleotide sequence for the ELF3 promoter disclosed in the present invention, as well as variants and fragments thereof, are useful in the genetic manipulation of any plant when assembled with a DNA construct such that the promoter sequence is operably linked to a nucleotide sequence encoding a heterologous protein of interest. In this manner, the nucleotide sequence of the ELF3 promoter of the invention is provided in expression cassettes along with heterologous nucleotide sequences for expression in the plant of interest.

The promoter for the ELF3 gene may regulate expression of operably linked nucleotide sequences in an inducible manner. That is, expression of the operably linked nucleotide sequences in a plant cell may be induced in response to a stimulus. By "stimulus" is intended a chemical, which may be applied externally or may accumulate in response to another external stimulus; or other factor such as environmental cues, including but not limited to, light quality and light quantity.

Synthetic hybrid promoter regions are known in the art. Such regions comprise upstream promoter elements of one nucleotide sequence operably linked to the promoter element of another nucleotide sequence. In an embodiment of the invention, heterologous gene expression is controlled by a synthetic hybrid promoter comprising the ELF3 promoter sequence of the invention, or a variant or fragment thereof, operably linked to upstream promoter element(s) from a heterologous promoter. Upstream promoter elements have been identified and may be used to generate a synthetic promoter. See, for example, Rushton, et al., (1998) *Curr. Opin. Plant Biol.* 1:311-315. Alternatively, a synthetic ELF3 promoter sequence may comprise duplications of the upstream promoter elements found within the ELF3 promoter sequence. Such elements include the six sequence motifs with approximately 50% identity to the "evening element" that are present within the upstream ZM-ELF3 sequence as noted herein above (FIG. 3). It is recognized that the promoter sequence of the invention may be used with its native ELF3 coding sequence. A DNA construct comprising the ZM-ELF3 promoter operably linked with its native ELF3 sequence may be used to transform any plant of interest to bring about a desired phenotypic change, such as inhibition of the shade-avoidance response and increased tolerance to plant density. Where the promoter and its native gene are naturally occurring within the plant, i.e., in maize, transformation of the plant with these operably linked sequences also results in either a change in phenotype, such as inhibition of the shade-avoidance response and increased tolerance to plant density, or the insertion of operably linked sequences within a different region of the chromosome thereby altering the plant's genome.

In another embodiment of the invention, expression cassettes will comprise a transcriptional initiation region comprising the ZM-ELF3 promoter nucleotide sequence disclosed herein, or variant or fragment thereof, operably linked to the heterologous nucleotide sequence whose expression is to be controlled by the ZM-ELF3 promoter of the invention.

The promoter nucleotide sequence and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

EXPERIMENTAL

Example 1

Identification and Cloning of ZM-ELF3 and bHLH-041 Genes

Activation tagging can be used to identify genes with the ability to affect a trait of interest. Insertions of transcriptional enhancer elements can dominantly activate and/or elevate the expression of nearby endogenous genes. By making a large population with these enhancer elements randomly inserted throughout the genome, one can assess the ability of nearly every gene to modify the trait of interest. This approach has been successfully used in the model plant species *Arabidopsis thaliana*. (Weigel, et al., 2000 *Plant Physiol.* 122:1003-1013). Isolation of genes associated with density response followed established protocols for activation tagging (Aukerman and Sakai (2003) *Plant Cell* 15(11):2730-2741).

An 18.4 kb T-DNA based binary construct, pHSbarENDs, that contains four multimerized enhancer elements derived from the Cauliflower Mosaic Virus 35S promoter, corresponding to nucleotides −341 to −64, as defined by Odell, et al., (1985) *Nature* 313:810-812. The construct also contains vector sequences (pUC9) to allow plasmid rescue, transposon sequences (Ds) to remobilize the T-DNA, and the bar gene to allow for glufosinate selection of transgenic plants. In principle, only the 10.8 kb segment from the right border (RB) to left border (LB) inclusive will be transferred into the host plant genome. Since the enhancer elements are located near the RB, they can induce cis-activation of genomic loci following T-DNA integration.

Two *Arabidopsis* activation-tagged populations were created by whole plant *Agrobacterium* transformation: Population 1 and Population 2.

For Population 1, the pHSbarENDs construct was transformed into *Agrobacterium tumefaciens* strain C58, grown in LB at 25° C. to OD600~1.0. Cells were then pelleted by centrifugation and resuspended in an equal volume of 5% sucrose/0.05% Silwet L-77 (OSI Specialties, Inc.). At early bolting, soil-grown *Arabidopsis thaliana* ecotype Col-0 plants were top-watered with the *Agrobacterium* suspension. A week later, the same plants were top-watered again with the same *Agrobacterium* strain in sucrose/Silwet. The plants were then allowed to set seed normally. The resulting $T_1$ seed were sown on soil, and transgenic $T_1$ seedlings were selected by spraying with glufosinate (Finale®; Agrevo; Bayer Environmental Science). $T_2$ seed was collected from approximately 35,000 individual glufosinate-resistant $T_1$ plants. $T_2$ plants were grown and equal volumes of $T_3$ seed from 96 separate $T_2$ lines were pooled, creating 360 sub-populations.

For Population 2, the plasmid was altered slightly to add restriction sites and renamed pHSbarENDs2. Transformation of the *Agrobacterium* strain and *Arabidopsis* plants were performed as described for Population 1.

A total of 100,000 glufosinate-resistant $T_1$ seedlings were selected. $T_2$ seed from each line was kept separate.

An activation tagging screen was performed with an *Arabidopsis* population containing transgenic inserts designed to activate proximal genes, in order to understand the response of plants to high density populations as well as to isolate genes that confer a density-insensitive phenotype. The activation tagged population was screened for variants in density response by planting seeds in soil at a density of approximately one plant per centimeter. Individual plants that differed significantly from their neighbors in terms of overall plant morphology and visual phenotype were selected at the flowering stage. Seed from these plants were re-screened in a second density experiment under similar conditions. Flanking sequence contiguous with the activation tag was isolated by plasmid rescue. Southern blotting, Northern blotting and PCR were used to verify that the variant activation-tagged line contained a single tag and that the closest flanking gene was activated. Several activation-tagged lines were isolated, the majority of which were late flowering. See Aukerman and Sakai (2003) *Plant Cell* 15(11):2730-2741.

Two genes were characterized from plants with altered phenotype when grown under high plant density. One gene corresponded to a circadian clock gene, ELF3, indicating that manipulation of genes involved in the circadian rhythm is a means to transgenically enhance yield of plants grown at high density. See FIG. 6.

The maize ELF3 homologue has been cloned and is disclosed herein (coding sequence shown in SEQ ID NO: 1, polypeptide shown in SEQ ID NOs: 2 and 3, upstream regulatory sequence shown in SEQ ID NO: 4). The *Arabidopsis* ELF3 (At-ELF3) protein sequence was used to identify maize homologues using tBLASTn (Gish and States (1993) *Nature Genet.* 3:266-272) to screen proprietary EST libraries. A partial maize sequence was identified with homology to At-ELF3, and the full length Zm-ELF3 was cloned by designing oligonucleotide primers to the N- and C-terminus of the protein and amplifying a complete coding sequence. The Zm-ELF3 gene was subsequently cloned into a plant transformation vector and transferred into *Arabidopsis* by the floral dip method (Clough and Bent (1998) *Plant Journal* 16(6):735-743).

The second activation-tagged line had a density hypersensitive response: plants were less vigorous under high density, but largely unchanged in low density. Cloning of the gene from this activation-tagged line isolated an uncharacterized basic helix-loop-helix transcription factor, bHLH-041 (coding sequence shown in SEQ ID NO: 5, polypeptide shown in SEQ ID NO: 6; see also GenBank accession BAA97026). This class of transcription factors is involved in a large number of plant responses, including some members that directly interact with phytochromes, involved in light perception. *Arabidopsis* sequence contiguous with the activation tag was cloned by plasmid rescue and sequence analysis revealed the tag inserted 807 bp from the bHLH-041 translational start. Activation was confirmed in this line by RT-PCR.

Example 2

Overexpression of ZM-ELF3 in Transgenic *Arabidopsis* Confers Density Tolerance

A full-length ZM-ELF3 was over-expressed in transgenic *Arabidopsis* using the SCP promoter (U.S. Pat. No. 6,555,673). The plants were transformed using the floral dip method (Clough and Bent (1998) *Plant Journal* 16(6):735-743). In this manner, the plants were dipped in a culture of *Agrobacterium* transformed with a co-integrate vector containing the ZM-ELF3 gene. Transgenic plants were identified by glufosinate resistance and grown to the subsequent generation, where seed were collected. Several transgenic lines and wild-type (WT) plants were assayed for density tolerance by determining their yield and plant performance under high density planting. High density in this screen was one plant per $cm^2$, which is about four times the density of optimal *Arabidopsis* growth.

Figure 2B:
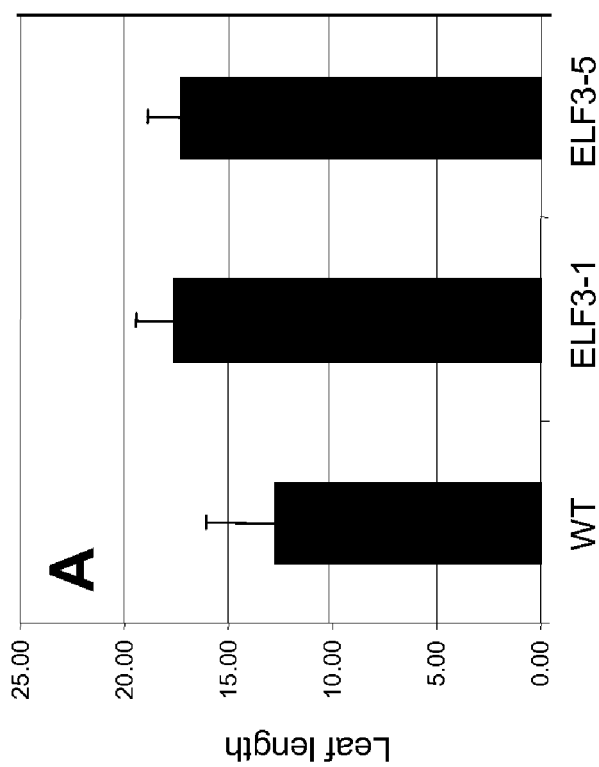

Transgenic plants were less susceptible to high plant density-induced decreases in leaf length (FIG. 2A) and leaf number at flowering (FIG. 2B).

ZmELF-3 transgenics were also evaluated in a delayed-planting experiment in which a grid of control plants were sown at high density. After ten days, the experimental material was planted amongst the control plants as an assessment of how well the plants could compete with neighboring plants further ahead in development. The activation-tagged line overexpressing ZmELF3 produced plants that were larger and had a more vigorous phenotype than the wild-type.

Example 3

Transformation and Regeneration of Transgenic Maize Plants Overexpressing the ZM-ELF3 Protein Immature maize embryos from greenhouse donor plants are bombarded with a plasmid containing the ZM-ELF3 nucleotide sequence of SEQ ID NO: 1 or 2 operably linked to the maize ubiquitin-1 (UBI1) promoter and the selectable marker gene PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the ZM-ELF3 nucleotide sequence of SEQ ID NO: 1 or 2 operably linked to the maize ubiquitin-1 (UBI1) promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored for density tolerance by determining their yield and plant performance under high density planting.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 4

Overexpression of ZM-ELF3 in Transgenic Maize

A full-length ZM-ELF3 is over-expressed in transgenic maize. For *Agrobacterium*-mediated transformation of maize with the ZM-ELF3 nucleotide sequence (SEQ ID NO: 1 or 2), the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the ZM-ELF3 nucleotide sequence of SEQ ID NO: 1 or 2 to at least one cell of at least one of the immature embryos (step 1: the infection step). The embryos are co-cultured for a time with the *Agrobacterium* (step 2: the co-cultivation step). Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Next, inoculated embryos are cultured on medium containing a selective agent and growing transformed callus is recovered (step 4: the selection step). The callus is then regenerated into plants (step 5: the regeneration step), and calli grown on selective medium are cultured on solid medium to regenerate the plants. Effect of overexpression of the ZM-ELF3 protein on plant density response is evaluated by determining transgenic plant yield and plant performance under high density planting.

Example 5

Soybean Embryo Transformation for Overexpression of ZM-ELF3 Culture Conditions

Soybean embryogenic suspension cultures (cv. Jack) are maintained in 35 ml liquid medium SB196 (see, recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein, et al., (1987) *Nature* 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the ZM-ELF3 nucleotide sequence of SEQ ID NO: 1 or 2, operably linked to the promoter of interest, and the selectable marker gene are used for bombardment. Plasmid DNA for bombardment are routinely prepared and purified using the method described in the Promega™ Protocols and Applications Guide, Second Edition (page 106). Fragments of the plasmids carrying the ZM-ELF3 nucleotide sequence of SEQ ID NO: 1 or 2, operably linked to the promoter of interest, and the selectable marker gene are obtained by gel isolation of double digested plasmids. In each case, 100 µg of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the ZM-ELF3 nucleotide sequence of SEQ ID NO: 1 or 2, operably linked to the promoter of interest, and the selectable marker gene are cut from the agarose gel. DNA is purified from the agarose using the GELase digesting enzyme following the manufacturer's protocol.

A 50 µl aliquot of sterile distilled water containing 3 mg of gold particles is added to 5 µl of a 1 µg/µl DNA solution (either intact plasmid or DNA fragment prepared as described above), 50 µl 2.5M CaCl$_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e., per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos are selected either using hygromycin (when the hygromycin phosphotransferase, HPT, gene is used as the selectable marker) or chlorsulfuron (when the acetolactate synthase, ALS, gene is used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post-selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post-selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2 s$. After this time embryo clusters are removed to a solid agar media, SB166, for 1-2 weeks. Clusters are then subcultured to medium SB103 for 3 weeks. During this period, individual embryos can be removed from the clusters and screened for ZM-ELF3 expression. It should be noted that any detectable phenotype, resulting from the expression of the genes of interest, could be screened at this stage.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted and the effect of overexpression of the ZM-ELF3 protein on plant density response is evaluated by determining transgenic plant yield and plant performance under high density planting.

| Media Recipes | |
|---|---|
| SB 196 - FN Lite liquid proliferation medium (per liter) - | |
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| $KNO_3$ | 2.83 gm |
| $(NH_4)_2SO_4$ | 0.463 gm |
| Asparagine | 1.0 gm |
| Sucrose (1%) | 10 gm |
| pH 5.8 | |

| FN Lite Stock Solutions | | | |
|---|---|---|---|
| Stock # | | 1000 ml | 500 ml |
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL—Cat# 11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat# 11117-066); 1 ml B5 vitamins 1000× stock; 60 g maltose; 750 mg $MgCl_2$ hexahydrate; 5 g activated charcoal; pH 5.7; and, 2 g gelrite.

SB 103 solid medium (per liter) comprises: 1 pkg. MS salts (Gibco/BRL—Cat# 11117-066); 1 ml B5 vitamins 1000× stock; 60 g maltose; 750 mg $MgCl_2$ hexahydrate; pH 5.7; and, 2 g gelrite.

SB 71-4 solid medium (per liter) comprises: 1 bottle Gamborg's B5 salts w/sucrose (Gibco/BRL—Cat# 21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20° C. comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide.

Example 6

Sunflower Transformation

Sunflower meristem tissues are transformed with an expression cassette containing the ZM-ELF3 nucleotide sequence of SEQ ID NO: 1 or 2 operably linked to the promoter of interest as follows (see also, European Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard (1980) *Emergent Techniques for the Genetic Improvement of Crops* University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ZM-ELF3 nucleotide sequence of SEQ ID NO: 1 or 2 operably linked to the promoter of interest is introduced into *Agrobacterium* strain EHA105 via freeze-thawing as described by Holsters, et al., (1978) *Mol. Gen. Genet.* 163: 181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for ZM-ELF3 activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by ZM-ELF3 activity analysis of leaf extracts while transgenic seeds harvested from NPTII-positive $T_0$ plants are identified by ZM-ELF3 activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for ZM-ELF3 activity using assays known in the art. After positive (i.e., for ZM-ELF3 expression) explants are identified, those shoots that fail to exhibit ZM-ELF3 activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for ZM-ELF3 expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

The articles "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for improving performance of a plant grown in high population density conditions, comprising
   (1) transforming a plant cell with a construct comprising an ELF3 polynucleotide; and
   (2) regenerating a plant from said transformed cell wherein the ELF3 polynucleotide is selected from the group consisting of:
   (a) the nucleotide sequence set forth in SEQ ID NO:1 or SEQ ID NO:2;
   (b) a nucleotide sequence encoding a polypeptide comprising the amino acid sequence of SEQ ID NO:3;
   (c) a nucleotide sequence which is at least 95% identical to the sequence set forth in SEQ ID NO:1 or SEQ ID NO:2; and
   (d) a nucleotide sequence encoding a polypeptide with an amino acid sequence which is at least 95% identical to SEQ ID NO:3,
   wherein expression of the nucleotide sequence in a plant results in greater leaf length and/or greater leaf number at flowering when grown under high population density compared to a plant not transformed with said nucleotide sequence and grown under the same conditions.

2. The method of claim 1, wherein said polynucleotide is operably linked to a promoter selected from the group consisting of a constitutive promoter, a leaf-preferred promoter, a light-regulated promoter, and a circadian-clock-regulated promoter.

3. An isolated polynucleotide comprising a nucleotide sequence selected from the group consisting of:
   (a) the nucleotide sequence set forth in SEQ ID NO:1 or SEQ ID NO:2;
   (b) a nucleotide sequence encoding a polypeptide comprising the amino acid sequence of SEQ ID NO:3;
   (c) a nucleotide sequence which is at least 95% identical to the sequence set forth in SEQ ID NO:1 or SEQ ID NO:2; and
   (d) a nucleotide sequence encoding a polypeptide with an amino acid sequence which is at least 95% identical to SEQ ID NO:3,
   wherein expression of the nucleotide sequence in a plant results in greater leaf length and/or greater leaf number at flowering when grown under high population density compared to a plant not transformed with said nucleotide sequence and grown under the same conditions.

4. An expression cassette comprising the polynucleotide of claim 3 operably linked to a promoter that drives expression in a plant cell.

5. A plant comprising the expression cassette of claim 4.

6. The plant of claim 5, wherein said plant is a monocot.

7. The plant of claim 6, wherein said monocot is maize, wheat, rice, barley, sorghum, or rye.

8. The plant of claim 5, wherein said plant is a dicot.

9. The plant of claim 8, wherein said dicot is soybean, *Brassica*, sunflower, cotton, or alfalfa.

10. A seed of the plant of claim 5, wherein said seed comprises said expression cassette.

11. An isolated polynucleotide comprising a nucleotide sequence of SEQ ID NO: 1 or SEQ ID NO: 2 or a nucleotide sequence encoding an amino acid sequence of SEQ ID NO: 3.

12. An expression cassette comprising the polynucleotide of claim 11 operably linked to a heterologous promoter sequence.

13. A transformed plant comprising the expression cassette of claim 12.

\* \* \* \* \*